(12) United States Patent
Chernukhin et al.

(10) Patent No.: US 9,950,280 B2
(45) Date of Patent: Apr. 24, 2018

(54) METHODS AND DEVICES FOR CHROMATIN IMMUNOPRECIPITATION ASSAYS

(71) Applicant: Porvair Filtration Group Limited, Fareham Hampshire (GB)

(72) Inventors: Igor Chernukhin, Colchester (GB); Elena Klenova, Near Manningtree Essex (GB); David Cowieson, Wrexham (GB); Samantha Brown, Ellesmere Shropshire (GB)

(73) Assignee: Porvair Filtration Group Limited, Fareham Hampshire (GB)

( * ) Notice: Subject to any disclaimer, the term of this patent is extended or adjusted under 35 U.S.C. 154(b) by 0 days.

(21) Appl. No.: 15/299,411

(22) Filed: Oct. 20, 2016

(65) Prior Publication Data
US 2017/0100683 A1    Apr. 13, 2017

Related U.S. Application Data

(62) Division of application No. 13/992,125, filed as application No. PCT/GB2011/052419 on Dec. 7, 2011, now Pat. No. 9,523,681.

(30) Foreign Application Priority Data

Dec. 10, 2010  (GB) .................................. 1021028.4
Mar. 23, 2011  (GB) .................................. 1104861.8

(51) Int. Cl.
*B01D 15/38*     (2006.01)
*G01N 33/543*    (2006.01)
*C12Q 1/68*      (2018.01)
*B01J 20/286*    (2006.01)

(52) U.S. Cl.
CPC ........ *B01D 15/3809* (2013.01); *B01J 20/286* (2013.01); *C12Q 1/6804* (2013.01); *G01N 33/54306* (2013.01); *G01N 33/54366* (2013.01); *B01J 2220/82* (2013.01)

(58) Field of Classification Search
None
See application file for complete search history.

(56) References Cited

U.S. PATENT DOCUMENTS

| | | | |
|---|---|---|---|
| 5,972,643 | A | 10/1999 | Lobanenkov et al. |
| 6,187,598 | B1 * | 2/2001 | May ................. G01N 33/54386 422/423 |
| 6,221,655 | B1 | 4/2001 | Fung et al. |
| 9,523,681 | B2 * | 12/2016 | Chernukhin ....... B01D 15/3809 |
| 2002/0064413 | A1 | 5/2002 | Cowieson |
| 2002/0192667 | A1 | 12/2002 | Kojima et al. |
| 2005/0032116 | A1 | 2/2005 | Nelson et al. |
| 2006/0118491 | A1 | 6/2006 | Gjerde et al. |
| 2006/0198765 | A1 | 9/2006 | Gjerde et al. |
| 2007/0106071 | A1 | 5/2007 | Yamashita et al. |
| 2007/0243549 | A1 | 10/2007 | Bischoff |
| 2009/0098020 | A1 | 4/2009 | Davis et al. |
| 2010/0047921 | A1 | 2/2010 | Suzuki et al. |
| 2010/0203335 | A1 | 8/2010 | Koizumi et al. |

FOREIGN PATENT DOCUMENTS

| | | | |
|---|---|---|---|
| EP | 0441660 | | 2/1991 |
| GB | 2369796 | | 6/2002 |
| JP | 2006-026607 | A | 2/2006 |
| JP | 2007-124952 | A | 5/2007 |
| JP | 2002-360245 | A | 12/2012 |
| WO | 03/014205 | A1 | 2/2003 |
| WO | 2005/018803 | | 3/2005 |
| WO | WO 2005/018803 | A1 * | 3/2005 ............. B01J 20/32 |
| WO | 2007/015502 | | 2/2007 |
| WO | 2008/066868 | | 6/2008 |
| WO | 2009/056339 | A1 | 5/2009 |
| WO | 2009/134814 | | 11/2009 |

OTHER PUBLICATIONS

Dasgupta et al. (Methods in Molecular Biology, vol. 383, pp. 135-152, 2007).*
Flanagin et al. (Nucleic Acids Research, 2008, vol. 36, No. 3, pp. 1-9) i.*
Maggio (Immunoenzyme technique I, CRC press _ 1980, pp. 186-187).*
Aparicio et al., "Chromatin immunoprecipitation for determining the association of proteins with specific genomic sequences in vivo," Current Protocols in Cell Biology, Chapter 17:Unit 17.7 (2004).
Bell et al. "Methylation of a CTCF-dependent boundary controls imprinted expression of the Igf2 gene," Nature, 405 (6785):482-485 (2000).
Bulyk, "DNA microarray technologies for measuring protein-DNA interactions," Current Opinion in Biotechnology, 17 (4):422-430 (2006).
Wilson et al., "HDAC4 promotes growth of colon cancer cells via repression of p21," Mol. Biol. Cell, 19:4062-4075 (2008).
Chernukhin et al., "CTCF interacts with and recruits the largest subunit of RNA polymerase II to CTCF target sites genome-wide," Molecular and Cellular Biology, 27:1631-1648 (2007).
Collas et al., "Chop it, ChIP it, check it: the current status of chromatin immunoprecipitation," Frontiers in Bioscience : A Journal and Virtual Library, 13:929-943 (2008).
Wu et al., "Automated microfluidic chromatin immunoprecipitation from 2,000 cells," Lab Chip., 9(10):1365-1370 (2009).
Cuddapah et al., "Global analysis of the insulator binding protein CTCF in chromatin barrier regions reveals demarcation of active and repressive domains," Genome Research, 19(1):24-32 (2009).

(Continued)

*Primary Examiner* — Lisa V Cook
(74) *Attorney, Agent, or Firm* — Morgan, Lewis & Bockius LLP

(57) ABSTRACT

The invention provides methods and devices for isolating chromatin from liquid samples. The devices have a rigid porous matrix on which a ligand is immobilized, with the ligand binding to a protein associated with the chromatin.

19 Claims, 11 Drawing Sheets

(56) References Cited

OTHER PUBLICATIONS

Dahl et al., "Fast genomic muChIP—chip from 1,000 cells," Genome Biology, 10(2):R13 (2009).
Dahl et al., "MicroChIP: chromatin immunoprecipitation for small cell numbers," Methods in Molecular Biology, 567: 59-74 (2009).
Dasgupta et al., "Chromatin immunoprecipitation assays: molecular analysis of chromatin modification and gene regulation," Methods in Molecular Biology, 383:135-152 (2007).
Wu et al., "ChIP—chip comes of age for genomewide functional analysis," Cancer Research, 66:6899-6902 (2006).
Farrell et al., "Conserved CTCF insulator elements flank the mouse and human beta-globin loci," Mol. Cell. Biol., 22 (11):3820-3831 (2002).
Filippova et al., "CTCF-binding sites flank CTG/CAG repeats and form a methylation-sensitive insulator at the DM1 locus," Nature Genetics, 28(4):335-343 (2001).
Filippova, "Genetics and epigenetics of the multifunctional protein CTCF," Curr. Top. Dev. Biol., 80:337-60 (2008).
Flanagin et al., "Microplate-based chromatin immunoprecipitation method, Matrix ChIP: a platform to study signaling of complex genomic events," Nucleic Acids Research, 36(3):e17 (2008).
Frank et al., "Binding of c-Myc to chromatin mediates mitogen-induced acetylation of histone H4 and gene activation," Genes & Development, 15(16): 2069-2082 (2001).
Yu et al., "Poly(ADP-ribosyl)ation regulates CTCF-dependent chromatin insulation," Nature Genetics, 36 (10):1105-1110 (2004).
Hage, "Affinity chromatography: a review of clinical applications," Clinical Chemistry, 45(5): 593-615 (1999).
Kim et al., "Analysis of the vertebrate insulator protein CTCF-binding sites in the human genome," Cell, 128 (6):1231-1245 (2007).
Kim et al., "Hypoxia-inducible factor 1 and dysregulated c-Myc cooperatively induce vascular endothelial growth factor and metabolic switches hexokinase 2 and pyruvate dehydrogenase kinase 1," Mol. Biol. Cell, 27(21):7381-7393 (2007).
Klenova et al., "The novel BORIS + CTCF gene family is uniquely involved in the epigenetics of normal biology and cancer," Seminars in Cancer Biology, 12(5):399-414 (2002).
Kuo et al., "In vivo cross-linking and immunoprecipitation for studying dynamic Protein:DNA associations in a chromatin environment," Methods: A Companion to Methods in Enzymology, 19(3):425-433 (1999).
Lutz et al., "Thyroid hormone-regulated enhancer blocking: cooperation of CTCF and thyroid hormone receptor," EMBO J., 22(7):1579-1587 (2003).
Marguet et al., "Protection of DNA by salts against thermodegradation at temperatures typical for hyperthermophiles," Extremophiles: Life Under Extreme Conditions, 2(2):115-122 (1998).
Massie et al., "ChIPping away at gene regulation," EMBO Rep, 9(4):337-343 (2008).
O'Neill et al., "Immunoprecipitation of native chromatin: NChIP," Methods: A Companion to Methods in Enzymology, 31 (1):76-82 (2003).
Ohlsson et al., "CTCF is a uniquely versatile transcription regulator linked to epigenetics and disease," Trends in Genetics, 17(9):520-527 (2001).
Parelho et al., "Cohesins functionally associate with CTCF on mammalian chromosome arms," Cell, 132(3):422-433 (2008).
Schmidt et al., "ChIP-seq: using high-throughput sequencing to discover protein-DNA interactions," Methods, 48 (3):240-248 (2009).
Takai et al., "Large scale mapping of methylcytosines in CTCF-binding sites in the human H19 promoter and aberrant hypomethylation in human bladder cancer," Human Molecular Genetics, 10(23):2619-2626 (2001).
Toniolo et al., "The CpG island in the 5' region of the G6PD gene of man and mouse," Gene, 102(2):197-203 (1991).
Farrar, "Mutational Analysis of the Poly(ADP-Ribosyl)ation Sites of the Transcription Factor CTCF Provides an Insight into Mechanism of Its Regulation by Poly(ADP-Ribosyl)ation," Molecular and Cellular Biology, 30(5):1199-1216 (2010).
Collas, "The Current State of Chromatin Immunoprecipitation," Molecular Biotechnology, 45(1): 87-100 (2010).
GE Healthcare: nProtein A Sepharose 4 Fast Flow, http://ww/gelifesciences.com/aptrix/upp00919.nsf/Contenl/C84F651DD17D665FC125775000828DBC/$file/18112519AD.pdf, pp. 1-4 (2007).
Chernukhin, "BioVyon Protein A, an Alternative Solid-Phase Affinity Matrix for Chromatin Immunoprecipitation," Analytical Biochemistry, 412(2): 183-188 (2011).
International Search Report for Application No. PCT/GB2011/052419, dated Apr. 13, 2012.
Maggio, Immunoenzyme Technique I, CRC Press, pp. 186-187 (1980).
Office Action issued in corresponding Japanese Patent Application No. 2013-542607 dated Sep. 7, 2015 (see partial translation).
Search Report issued in corresponding Japanese Patent Application No. 2013-542607 dated Sep. 4, 2015.

* cited by examiner

SEQUENCE LISTING

<160> NUMBER OF SEQ ID NOS: 14

<210> SEQ ID NO 1
<211> LENGTH: 19
<212> TYPE: DNA
<213> ORGANISM: Artificial Sequence
<220> FEATURE:
<223> OTHER INFORMATION: GAPDH (promoter, TATA-box) mouse forward primer

<400> SEQUENCE: 1
tcctgcaatg atagactag                                                19

<210> SEQ ID NO 2
<211> LENGTH: 20
<212> TYPE: DNA
<213> ORGANISM: Artificial Sequence
<220> FEATURE:
<223> OTHER INFORMATION: GAPDH (promoter, TATA-box) mouse reverse primer

<400> SEQUENCE: 2
ctgccaaaca cgttcacaga                                               20

<210> SEQ ID NO 3
<211> LENGTH: 22
<212> TYPE: DNA
<213> ORGANISM: Artificial Sequence
<220> FEATURE:
<223> OTHER INFORMATION: N-site-Myc human forward primer

<400> SEQUENCE: 3
acctgacccc cgccctcgtt ga                                            22

<210> SEQ ID NO 4
<211> LENGTH: 22
<212> TYPE: DNA
<213> ORGANISM: Artificial Sequence
<220> FEATURE:
<223> OTHER INFORMATION: N-site-Myc human reverse primer

<400> SEQUENCE: 4
ctctactggc agcagagatc at                                            22

<210> SEQ ID NO 5
<211> LENGTH: 20
<212> TYPE: DNA
<213> ORGANISM: Artificial Sequence
<220> FEATURE:
<223> OTHER INFORMATION: Beta-Globin human (5'HS5) human forward primer

<400> SEQUENCE: 5
ttgggtttga atcgatacgc                                               20

<210> SEQ ID NO 6
<211> LENGTH: 20
<212> TYPE: DNA
<213> ORGANISM: Artificial Sequence
<220> FEATURE:
<223> OTHER INFORMATION: Beta-Globin human (5'HS5) human reverse primer

<400> SEQUENCE: 6
gcacccacct tcaatcaaaa                                               20

<210> SEQ ID NO 7
<211> LENGTH: 18
<212> TYPE: DNA
<213> ORGANISM: Artificial Sequence

```
<220> FEATURE:
<223> OTHER INFORMATION: DM1 Human (CTCF site 1) forward primer

<400> SEQUENCE: 7
gcctgccagt tcacaacc                                                    18

<210> SEQ ID NO 8
<211> LENGTH: 19
<212> TYPE: DNA
<213> ORGANISM: Artificial Sequence
<220> FEATURE:
<223> OTHER INFORMATION: DM1 Human (CTCF site 1) reverse primer

<400> SEQUENCE: 8
cattcccggc tacaaggac                                                   19

<210> SEQ ID NO 9
<211> LENGTH: 19
<212> TYPE: DNA
<213> ORGANISM: Artificial Sequence
<220> FEATURE:
<223> OTHER INFORMATION: H19 ICR (CTCF site 1) human forward primer

<400> SEQUENCE: 9
cccatcttgc tgacctcac                                                   19

<210> SEQ ID NO 10
<211> LENGTH: 20
<212> TYPE: DNA
<213> ORGANISM: Artificial Sequence
<220> FEATURE:
<223> OTHER INFORMATION: H19 ICR (CTCF site 1) human reverse primer

<400> SEQUENCE: 10
agacctggga cgtttctgtg                                                  20

<210> SEQ ID NO 11
<211> LENGTH: 20
<212> TYPE: DNA
<213> ORGANISM: Artificial Sequence
<220> FEATURE:
<223> OTHER INFORMATION: PLK human forward primer

<400> SEQUENCE: 11
ttgcctttgc ggttctaaca                                                  20

<210> SEQ ID NO 12
<211> LENGTH: 20
<212> TYPE: DNA
<213> ORGANISM: Artificial Sequence
<220> FEATURE:
<223> OTHER INFORMATION: PLK human reverse primer

<400> SEQUENCE: 12
ggaattcctt cggggtttct                                                  20

<210> SEQ ID NO 13
<211> LENGTH: 20
<212> TYPE: DNA
<213> ORGANISM: Artificial Sequence
<220> FEATURE:
<223> OTHER INFORMATION: PIM human forward primer

<400> SEQUENCE: 13
ttgggtttga atcgatacgc                                                  20
```

```
<210> SEQ ID NO 14
<211> LENGTH: 18
<212> TYPE: DNA
<213> ORGANISM: Artificial Sequence
<220> FEATURE:
<223> OTHER INFORMATION: PIM human reverse primer

<400> SEQUENCE: 14
ctctcgcggt cagaatgg                                                      18
```

METHODS AND DEVICES FOR CHROMATIN IMMUNOPRECIPITATION ASSAYS

SEQUENCE LISTING SUBMISSION VIA EFS-WEB

A computer readable text file, entitled "067024-5015-01-SequenceListing.txt," created on or about 18 Oct. 2016, with a file size of about 4 kb contains the sequence listing for this application and is hereby incorporated by reference in its entirety.

FIELD

The present invention relates to a chromatin immunoprecipitation assay method, and a separation column for use in such a method.

BACKGROUND

Chromatin immunoprecipitation (ChIP) is an important technique used in the study of DNA/protein interactions. An advantage of ChIP is that it can be used for analysing the association of specific proteins, or their modified isoforms, with defined genomic regions. A review of existing ChIP technology is provided in O'Neill et al. (2003) "Immunoprecipitation of native chromatin, NChIP", Methods: A Companion to Methods in Enzymology 31:76-82. ChIP may be used to determine whether proteins such as transcription factors and modified histones bind to a particular region on the endogenous chromatin of living cells or tissues.

In a ChIP assay, fragments of the DNA-protein complex (i.e. the chromatin) are prepared in such a way so as to retain the specific DNA-protein interactions. These chromatin fragments can then be immunoprecipitated using an antibody against the protein present in the complex. The isolated chromatin fraction can then be treated to separate the DNA and protein components. The identity of DNA fragments isolated in connection with a particular protein (i.e. the protein against which the antibody used for immunoprecipitation was directed) can then be determined by Polymerase Chain Reaction (PCR), Real Time PCR, hybridization on microarrays, direct sequencing or other technologies used for identification of DNA fragments of defined sequence.

Hence, a chromatin immunoprecipitation assay typically involves the following five key steps: (i) preparation of chromatin to be analysed from cells; (ii) immunoprecipitation of chromatin using an antibody; (iii) isolation of the precipitated chromatin fragments; (iv) DNA recovery from the precipitated product; and (v) DNA analysis.

The ChIP technique has two major variants that differ primarily in how the starting (input) chromatin is prepared. The first variant (designated NChIP) uses native chromatin prepared by micrococcal nuclease digestion of cell nuclei by standard procedures. The second variant (designated XChIP) uses chromatin cross-linked by addition of formaldehyde to growing cells, prior to fragmentation of chromatin, usually by sonication. Some workers have used mild formaldehyde cross-linking followed by nuclease digestion, and UV irradiation has been successfully employed as an alternative cross-linking technique.

Typically the immunoprecipitation of chromatin fragments is performed using an antibody specific to the protein of interest which is bound to DNA. The antibody-bound chromatin fragments may be isolated from the sample using a solid phase. For instance, the antibody itself may be directly linked to a solid phase such as agarose or magnetic beads which is then contacted with the chromatin. Alternatively, an antibody free in solution may be applied to the chromatin-containing sample, and then antibody-bound chromatin fragments isolated using an agent such as protein A, protein G or an anti-immunoglobulin antibody conjugated to the solid phase.

The solid phase which is used in this step is typically either a gel-type structure (usually based on the carbohydrate agarose) or magnetic beads (usually based on polymethacrylate type polymers). In either case the solid phase is dispersed within the liquid sample, and must be separated from the sample by some means after binding of the chromatin to the solid phase. A gel (e.g. agarose) can be spun down in a centrifuge to form a pellet which can then be separated from the liquid sample by aspiration. Magnetic beads are typically separated by using a magnet to pull the beads to the side of the vessel while the liquid sample is aspirated from the vessel.

In the case of agarose gels, the pellet formation and aspiration steps need to be repeated several times to remove all traces of the sample, which is inconvenient and slow. Although the use of magnetic beads is typically faster and more convenient than using agarose, the separation step using a magnet and aspiration still requires considerable skill and can be time-consuming. Moreover, both methods involve loss of product at various stages which can accumulate through the whole process. The handling steps necessary with gels and beads make it difficult to obtain high DNA recovery with good purity, as well as good reproducibility between assays. Agarose gels and magnetic beads are prone to non-specific binding of DNA and proteins, and it is difficult to provide adequate washing steps to reduce the resulting background signal. Thus standard ChIP assays typically require a large amount of sample while providing insufficient specificity in terms of the isolated DNA product. Such methods are also difficult to automate and unsuited to high throughput screening applications.

Thus there is a need for improved chromatin immunoprecipitation assay methods which address one or more of the above problems. In particular, there is a need for methods and products for isolating chromatin from a sample which are sensitive, specific and convenient to use.

SUMMARY

Accordingly, in one embodiment the present invention provides a method for isolating chromatin from a sample, comprising a step of passing a liquid sample comprising chromatin through a rigid porous matrix on which a ligand is immobilized, wherein the ligand binds to a protein associated with the chromatin.

Preferably the rigid porous matrix comprises sintered thermoplastic polymer particles. In one embodiment, the rigid porous matrix is in the form of a filter disc or frit.

In one embodiment, the rigid porous matrix comprises a modified surface produced by chemical oxidation. Preferably the modified surface is produced by treatment with one or more oxidizing acids.

The rigid porous matrix may, for example, be contained within a separation column, preferably a spin column. In one embodiment, the column further comprises a hydrophobic matrix.

Preferably the liquid sample is drawn through the rigid porous matrix in a centrifuge, by gravity, or a vacuum.

In one embodiment, the liquid sample comprises chromatin to which an immunoglobulin is bound. The ligand may comprise, for example, an antibody, protein A or protein G.

The method preferably further comprises one or more steps selected from (i) passing a wash solution through the rigid porous matrix, (ii) separating nucleic acids present in the chromatin bound to the matrix from associated proteins and (iii) detecting a nucleic acid which was present in chromatin bound to the matrix.

In one embodiment, an array comprising a plurality of rigid porous matrices is provided, and each of a plurality of liquid samples is passed through a rigid porous matrix in the array. Preferably the array comprises a multiwell plate, each well within the plate comprising a separation column as defined above.

In another aspect, the invention provides a separation column comprising a chamber for holding a liquid sample comprising chromatin, and a rigid porous matrix on which a ligand is immobilized, wherein the ligand is capable of binding to a protein associated with the chromatin, and wherein the rigid porous matrix is positioned within the chamber such that the liquid sample can be passed through the rigid porous matrix.

In one embodiment, the rigid porous matrix comprises sintered thermoplastic polymer particles. Preferably the rigid porous matrix is in the form of a filter disc or frit.

In one embodiment, the rigid porous matrix comprises a modified surface produced by chemical oxidation. Preferably the modified surface is produced by treatment with one or more oxidizing acids.

In one embodiment, the rigid porous matrix is positioned above an effluent port of the column. Preferably the liquid sample held in the chamber can be passed through the rigid porous matrix and exit the column, thereby isolating chromatin from the liquid sample by binding of chromatin to the rigid porous matrix.

In one embodiment the column further comprises a collection vessel for receiving liquid which has passed through the rigid porous matrix and exited the column. The column may further comprise a hydrophobic matrix. Preferably the hydrophobic matrix is positioned between the rigid porous matrix and an effluent port of the column.

In one embodiment the separation column is a spin column. Preferably the ligand comprises an immunoglobulin, protein A or protein G.

In a further aspect, the invention provides an array comprising a plurality of separation columns as defined above. Preferably the array is in the form of a multiwell plate or filtration microplate.

In a further aspect, the invention provides a kit comprising a separation column as defined above, and one or more buffers, solutions or reagents suitable for performing a chromatin immunoprecipitation assay.

In a further aspect, the invention provides use of a separation column as defined above, for isolating chromatin from a liquid sample. Typically the separation column is used in a chromatin immunoprecipitation assay.

Embodiments of the present invention advantageously permit the isolation of chromatin fragments from a sample with high specificity and sensitivity. Moreover, by passing the sample through a rigid porous matrix, the method is much more convenient to use than conventional methods using agarose or magnetic beads.

BRIEF DESCRIPTION OF THE FIGURES

FIG. 2A. Real-time PCR analysis of ChIP assays with the mouse monoclonal anti-RNA Polymerase II antibody and TATA-box. The cross-linked cell lysates from NIH 3T3 mouse fibroblasts were used for ChIP with the mouse monoclonal anti-RNA Polymerase II antibody. Control samples were run in parallel and contained either no antibody, non-specific mouse IgG and anti-actin mouse monoclonal (irrelevant) antibody. The DNA recovered after ChIP procedures was amplified in a PCR reaction with primers overlapping the GAPDH TATA-box (see Table 1 for detail). FIG. 2B. Real-time PCR analysis of ChIP assays with the anti CTCF rabbit polyclonal antibody and different CTCF target sites (CTSs). The cross-linked cell lysates from MCF7 breast cancer cells were used for ChIP with the anti-CTCF rabbit polyclonal antibody. Control samples were run in parallel and contained either no antibody, non-specific rabbit IgG and anti-rabbit His-tag (irrelevant) antibody. The DNA recovered after ChIP procedures was amplified in a PCR reaction with primers overlapping six CTSs N-site Myc [10; 19], PIM [15], DM1 [20], β-globin [21], PLK[15] and H19 [22; 23] (see Table 1 for detail).

FIG. 5A: SEM of untreated BioVyon™ at a magnification of 2300× illustrating the smooth surface structure of the sintered particles with the pores formed between clearly shown. FIG. 5B: SEM of etched BioVyon™ at a magnification of 2300× illustrating the pitted surface structure of the sintered particles, which provides the additional surface area.

FIG. 6B. The BioVyon™-Protein A gravity flow columns. The columns have the same dimensions as a standard 1 ml Solid Phase Extraction (SPE) tube and contain rigid porous High Density Polyethylene (HDPE) frits approximately 6 mm in diameter by 2 mm long. Examples of a column with a single disc (top) and several stacked discs (bottom) are shown. FIG. 6C A spin column comprising a rigid porous matrix (in the form of a BioVyon™-protein A disc) positioned above the effluent port.

FIG. 7A. Analysis of the PCR products from ChIP DNA obtained using the protocol, which included different concentrations of SDS (0.1% or 0.2%) during the washing step with the High Salt (HS) Buffer: 0.1% SDS (or 0.2% SDS), 20 mM Tris/Hcl pH 8.0, 2 mM EDTA, 500 mM NaCl, 1% TRITON X100. The preblocking step was included in this protocol. The enrichment values are shown in the inserted table. FIG. 7B. Analysis of the PCR products from ChIP DNA obtained using the protocol, which included different numbers of washes (three and six) and also with or without a washing step containing LiCl buffer. Abbreviations: LS buffer (Low salt buffer): 10 mM Tris/Hepes pH8.0, 1 mM EDTA, 150 mM NaCl; MS buffer (Medium salt buffer): 0.1% SDS, 20 mM Tris/HCl pH8.0, 2 mM EDTA, 150 mM NaCl, 1% TRITON X100; HS buffer (High salt buffer): 0.1% SDS, 20 mM Tris/HCl pH8.0, 2 mM EDTA, 500 mM NaCl, 1% TRITON X100; LiCl buffer: 250 mM LiCl, 10 mM Tris/HCl pH8.0, 1 mM EDTA, 1% Na-deoxycholate.

DETAILED DESCRIPTION

Figure 1:
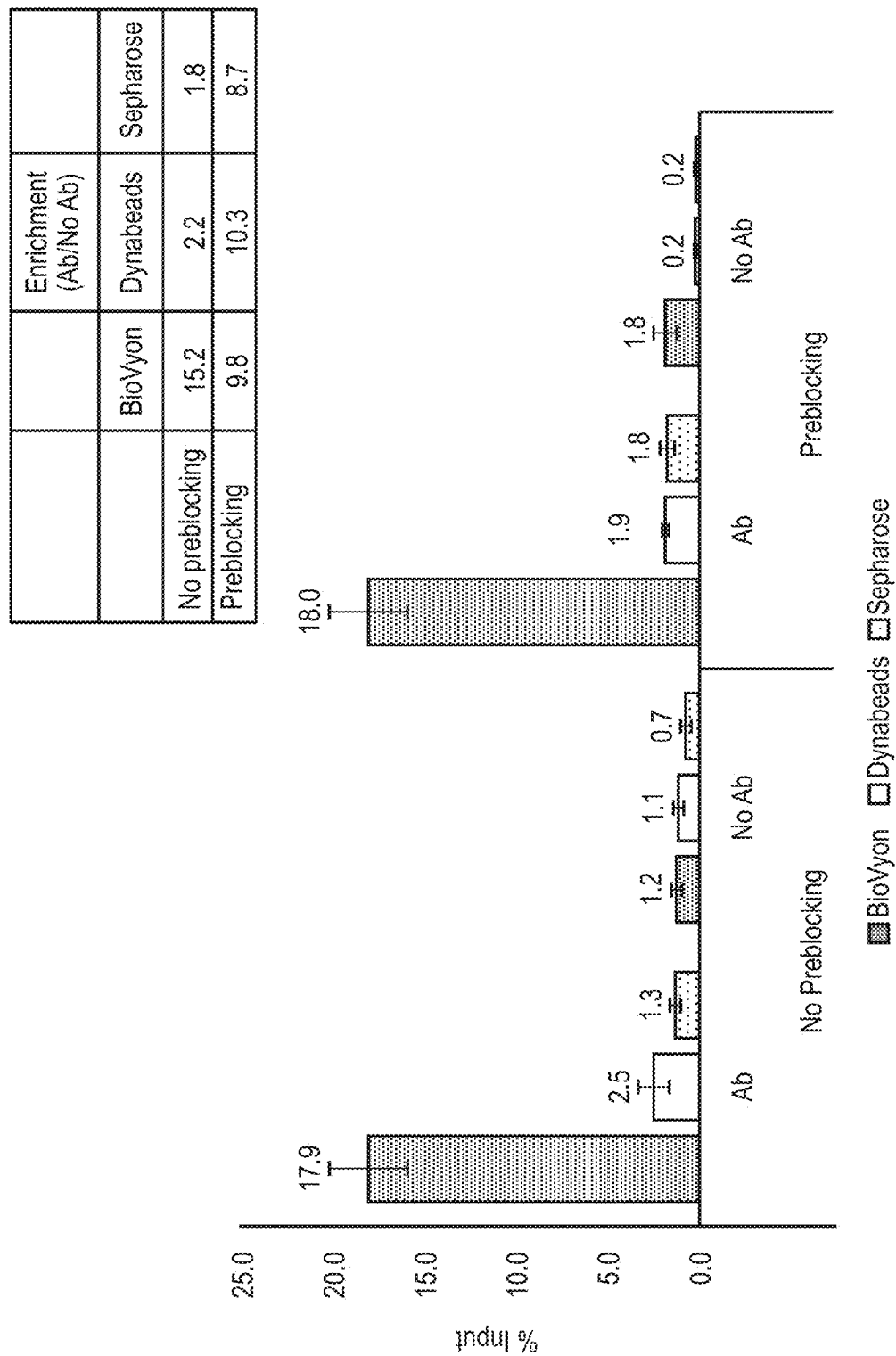
FIG. 1 Real-time PCR analysis of PCR products from optimization experiments for the pre-blocking step in ChIP assays using BioVyon™-Protein A (in gravity flow columns). ChIP assays with the mouse monoclonal antibodies against RNA Polymerase II were performed using cross-linked cell lysates obtained from NIH 3T3 mouse fibroblasts. The DNA recovered after ChIP procedures was PCR amplified with primers overlapping the GAPDH TATA-box (see Table 1 for detail). Three separate experiments were conducted, and quantification of three replicates of a typical experiment is shown. Preblocking of the BioVyon™-Protein A columns was performed with the preblocking solution containing LS ("Low salt") Buffer (0.1% SDS, 1% TRI-TONX-100, 2 mM EDTA, 20 mM Tris-HCl, pH 8, 150 mM NaCl)+1 mg/ml BSA+400 µg salmon sperm DNA) as described in the ChIP protocol for Protein A Sepharose®. The BioVyon™-Protein A columns were filled with the pre-blocking solution, incubated for 30 min at +40° C. and then drained. Ab=Antibody present, No Ab=No Antibody present. The enrichment values represent the ratio of the RT-PCR value of a ChIP assay with the antibody to the corresponding control (ChIP assay without the antibody); they are shown in the inserted table.

In one aspect, the present invention relates to a method of isolating chromatin from a sample. By "isolating chromatin" it is typically meant that chromatin becomes bound to the matrix, e.g. such that it can be conveniently separated from the liquid sample.

Chromatin

Chromatin consists of a complex of DNA and protein (primarily histone), and makes up the chromosomes found in eukaryotic cells. Chromatin occurs in two states, euchromatin and heterochromatin, with different staining properties, and during cell division it coils and folds to form the metaphase chromosomes. Chromatin is used herein to refer to any such complex of nucleic acid (typically DNA) and associated proteins, including chromatin fragments produced by fragmentation of chromosomes or other chromatin preparations.

Chromatin Immunoprecipitation

Typically the method is performed as part of a chromatin immunoprecipitation (ChIP) assay. The term "chromatin immunoprecipitation assay" is well known to a skilled person, and preferably comprises at least the following steps: (i) preparation of a liquid sample comprising chromatin to be analysed from cells; (ii) immunoprecipitation of the chromatin in the liquid sample onto the matrix using an antibody; and (iii) DNA recovery from the precipitated chromatin and (iv) DNA analysis. The ChIP assay may be NChIP or XChIP as described above.

Sample

The liquid sample may be prepared from any biological source which comprises chromatin, e.g. any preparation comprising cells. The cells may be derived from a tissue sample, or from cells grown in culture. Preferably the cells comprise mammalian cells, preferably human or mouse cells.

Typically, the method may be performed on a sample comprising chromatin from $10^3$ to $10^9$ cells, e.g. preferably less than $10^7$ cells, less than $10^6$ cells or less than $10^5$ cells, preferably about $10^4$ to $10^6$ cells. One cell typically contains about 6 µg ($6\times10^{12}$ g) DNA per cell and equal amounts of DNA and protein in chromatin. Thus the method may be performed, for example, on a sample comprising about 0.6 µg DNA, or 1.2 µg of chromatin (this equates to mass of DNA or chromatin in about 100,000 cells).

Chromatin Preparation

In embodiments of the present invention, a preparation comprising cells is subjected to a chromatin immunoprecipitation assay (ChIP). Typically chromatin is first extracted from the preparation to prepare a liquid sample comprising chromatin fragments.

In one embodiment, cells are first harvested from the preparation using standard techniques, from which nuclei may then be obtained. For example, the cells may be disrupted (e.g. using a cell lysis buffer or sonication), which results in the nuclei being released there from. Following release of the nuclei, the method preferably comprises a step of digesting the nuclei in order to release the chromatin, for example using micrococcal nuclease or further sonication.

In another embodiment, the method may comprise a step of cross-linking the chromatin. This may be achieved for any suitable means, for example, by addition of a suitable cross-linking agent, such as formaldehyde, preferably prior to fragmentation of the chromatin. Fragmentation may be carried out by sonication. However, formaldehyde may be added after fragmentation, and then followed by nuclease digestion. Alternatively, UV irradiation may be employed as an alternative cross-linking technique.

In one embodiment, cells or tissue fragments are first fixed with formaldehyde to crosslink protein-DNA complex. Cells can be incubated with formaldehyde at room temperature or at 37° C. with gentle rocking for 5-20 min, preferably for 10 min. Tissue fragments may need a longer incubation time with formaldehyde, for example 10-30 min, e.g. 15 min. The concentration of formaldehyde can be from 0.5 to 10%, e.g. 1% (v/v).

Once crosslinking reaction is completed, an inhibitor of crosslink agents such as glycine at a molar concentration equal to crosslink agent can be used to stop the crosslinking reaction. An appropriate time for stopping the crosslinking reaction may range from 2-10 min, preferably about 5 min at room temperature. Cells can then be collected and lysed with a lyses buffer containing a sodium salt, EDTA, and detergents such as SDS. Tissue fragments can be homogenized before lysing.

Cells or the homogenized tissue mixture can then be mechanically or enzymatically sheared to yield an appropriate length of the DNA fragment. Usually, 200-1000 bp of sheared chromatin or DNA is required for the ChIP assay. Mechanical shearing of DNA can be performed by nebulization or sonication, preferably sonication. Enzymatic shearing of DNA can be performed by using DNAse I in the presence of Mn salt, or by using micrococcal nuclease in the presence of Mg salt to generate random DNA fragments. The conditions of crosslinked DNA shearing can be optimized based on cells, and sonicator equipment or digestion enzyme concentrations.

In one embodiment, once DNA shearing is completed, cell debris can be removed by centrifugation, and supernatant containing DNA-protein complex is collected. The result is a liquid sample comprising chromatin fragments in which the protein is immobilized on the DNA (e.g. wherein the DNA and protein are cross-linked) which can be used in the present method. In an alternative embodiment, the centrifugation step may be omitted, i.e. the following steps are performed directly after DNA shearing.

Immunoprecipitation

Once the proteins have been immobilized on the chromatin, the protein-DNA complex may then be immunoprecipitated. Hence, once the sample comprising chromatin has been prepared, the method preferably comprises a step of immunoprecipitating the chromatin. Preferably immunoprecipitation is carried out by addition of a suitable antibody against a protein of interest which may be present in the chromatin.

In one embodiment, the antibody may be immobilized on the rigid porous matrix, i.e. the antibody is the ligand which binds to the protein associated with the chromatin. In this embodiment, the protein associated with the chromatin is the protein of interest, e.g. which is bound to DNA in the chromatin.

In an alternative embodiment, an antibody free in solution is first applied to the chromatin-containing sample. Antibody-bound chromatin fragments may then be isolated using an agent which binds the antibody, the agent being conjugated to the rigid porous matrix. In this embodiment, the ligand bound to the rigid porous matrix may be any agent which binds the antibody, such as protein A, protein G or an anti-immunoglobulin (e.g. anti-IgG) antibody. The protein associated with the chromatin is the antibody specific for the protein of interest.

The antibody may bind to any protein associated with the chromatin. In one embodiment, the antibody is immunospecific for non-histone proteins such as transcription factors, or other DNA-binding proteins. Alternatively, the antibody may be immunospecific for any of the histones H1, H2A, H2B, H3 and H4 and their various post-translationally modified isoforms and variants. Alternatively, the antibody may be immunospecific for enzymes involved in modification of chromatin, such as histone acetylases or deacetylases, or DNA methyltransferases. Furthermore, it will be appreciated that histones may be post-translationally modified in vivo, by defined enzymes, for example, by acetylation, methylation, phosphorylation, ADP-ribosylation, sumoylation and ubiquitination of defined amino acid residues. Hence, the antibody may be immunospecific for any of these post-translational modifications.

Rigid Porous Matrix

In embodiments of the present invention, the liquid sample comprising chromatin, optionally bound by an antibody, is passed through a rigid porous matrix.

Suitable matrices are known in the art. In one embodiment, the rigid porous matrix comprises sintered thermoplastic polymer particles, e.g. as described in WO 2005/018803. The matrix may have a modified surface which is chemically reactive or functionalized, e.g. which provides pendant functional groups which are suitable for attaching the ligand, optionally via a linker. The matrices of the invention are essentially rigid.

In one embodiment, the matrix comprises a thermoplastic polymer such as a polyolefin or a vinyl polymer. Examples of such polyolefins include polyethylene and polypropylene. Examples of vinyl polymers include polyvinyl acetate (PVA) and polyvinyl chloride (PVC). Preferred polymers include polyethylene or polypropylene, most preferably polyethylene. In other embodiments, the thermoplastic polymer may be polyvinylidene fluoride (PVDF), polytetrafluoroethylene (PTFE) or polyamide (Nylon).

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" also includes all possible geometric configurations of the molecule. These configurations include, inter alia, isotactic, syndiotactic, atactic and random symmetries.

In one embodiment, the thermoplastic polymer is polyethylene; or a copolymer or blend which comprises polyethylene, preferably at least 80% polyethylene, particularly preferably at least 90% polyethylene and most preferably at least 95% polyethylene.

Examples of usable polyethylenes include high density polyethylene and ultra high molecular weight polyethylene, as manufactured by Porvair Technology, UK, under the tradename "Vyon" or "BioVyon". The thermoplastic polymer may also comprise flow modifiers, additives, etc., as are usual in the art.

The thermoplastic polymer particles to be sintered to form the matrix will in general have a size in the range that is appropriate for the ultimate use of the matrix. The particles may be spherical, generally spherical or may be any other suitable regular or irregular shape. The person skilled in the art will appreciate that the rate of fluid passage through the matrix will be determined at least in part by the sizes of the particles which comprise the matrix and the conditions under which those particles are sintered. Other variables to be taken into account in this regard include the molecular size and other properties of any material which is linked to the matrix.

As used herein, the term "sintered thermoplastic polymer" refers to a number of thermoplastic polymer particles which generally have been coalesced into a single unit under the influence of heat and vibration, without actually liquefying the polymer. The matrix therefore comprises a plurality of fused thermoplastic polymer particles having a defined structure which is maintained upon the application of a fluid. The "sintered thermoplastic polymer" will also in general be essentially rigid due to the fused nature of the constituent particles, i.e. it will be essentially incompressible and it will not shrink or swell in aqueous solutions. However, some embodiments of the invention such as sheets or membranes which comprise the matrix of the invention may be flexible.

Methods of sintering thermoplastics are well known in the art. These include the methods disclosed in e.g. US2002/064413 and GB 2369796.

The pore size of matrix post-sintering may be predetermined during its manufacture to be appropriate for the desired use. In general, the sizes of the pores in the matrix may be 1-1000, μm, 1-500 μm, 500-1000 μm, 200-700 μm, 5-100 μm, 20-40 μm or 40-80 μm.

After sintering, the matrix is modified in order to provide a chemically-reactive surface, e.g. a functionalized surface, preferably an irregular surface. This modification increases the surface area of the matrix. It also provides functional groups on the surface which facilitate the attachment of the ligand. In other words, the chemically reactive surface is a modified surface which provides pendant functional groups which are suitable for attaching the ligand to the surface, optionally via a linker.

A number of techniques are known for the surface modification of thermoplastic polymers. Three preferred techniques which are usable in this regard are gas plasma amination, gamma-irradiation and chemical oxidation, as described in WO 2005/018803.

Preferably the matrix has a modified surface produced by chemical oxidation. Chemical oxidation techniques result in the creation of intermediate irregular reactive functions via the breaking of carbon bonds in the thermoplastic.

Preferably, the surface of the matrix is modified by treatment with one or more oxidizing acids, e.g. an acid selected from the group consisting of trifluoroacetic acid, trifluoromethane sulfonic acid, chromium trioxide and sulfuric acid; optionally in the presence of a peroxide salt such as $K_2Cr_2O_7$.

A number of strategies have been commonly employed for the chemical oxidation of thermoplastics. If modification of the thermoplastic surface only is desired, this can be achieved by relatively mild chemical oxidation using a peroxide salt and acid such as $K_2Cr_2O_7$ in $H_2SO_4$, without causing significant damage to the physical structure of the surface. Physical erosion of the thermoplastic (tunnels and holes inside the plastic material to increase its binding capacity, prior to modification of the surface of the plastic material) can be achieved by treatment of the plastic with more aggressive acid such as trifluoroacetic acid applied at higher concentrations and higher temperatures.

The types of the functional groups that are present on the surface of the matrix depend on the type of the reaction that is employed to generate them. In most cases, carboxyl or hydroxyl groups are produced. Aldehyde and keto groups can also be generated as side products of the reaction. Carboxyl or hydroxyl functions can be substituted by more stable and potentially reactive functions, for instance, amines. Amino groups can be chemically introduced directly onto the thermoplastic surface or attached via spacer molecules (linkers).

After the surface of the matrix has been functionalized, the surface may be reacted with one or more linkers or spacers. The function of such entities is (i) to facilitate the attachment of a desired ligand to the surface of the matrix and/or (ii) if desired, to allow the ligand to be placed at a certain distance away from the surface of the matrix.

Advantageously, the modified surface remains chemically inert thus significantly reducing the non-specific background binding. Linker technology helps to preserve to a large extent the native conformation of any immobilized proteins, and also any proteins which are purified on such matrices. Utilization of a non-cleavable linker on the matrix allows permanent covalent coupling of the protein to the matrix thus radically reducing leaching of any immobilized molecules from the matrix.

Preferably, a linker is bound to the surface of the matrix. Most preferably, the linker is bound to the surface of the matrix immediately after the surface has been modified.

The selection of an appropriate linker will be dependent on the surface functionalization of the matrix and the ligand intended to be bound to the matrix. Numerous such linkers are known in the art. In particular, reactions which may be employed for coupling polypeptide or DNA/RNA molecules to certain linkers or directly to solid supports are well known in the art. Conveniently, functional groups can be incorporated into a ligand during its chemical synthesis. Potential functional groups include ethers, esters, thiols, dialkylamides, hydrazides, diamines and many others. Appropriate linkers will be those that contain groups which are capable of reacting with one or more of the aforementioned functional groups. For example, a linker which utilizes the formation of thioether bond between the ligand and the linker could have the thiol group on one (ligand) end and bromoacetyl group on the other (linker).

Typically the ligand which is immobilized on the matrix is a biological molecule, commonly a protein (for example, an antibody, protein A or protein G). It is important to preserve the activity of the biological molecule once it is bound to the matrix. This restricts the choice of linker strategies, because non-denaturing (i.e. physiological or mild) conditions must be used to link the protein to the linker. Not all linkers can be used under such conditions. The biological activity of a protein might be dependent on the accessibility (to a substrate) of a particular functional group; such groups must therefore not be used to link the protein to the matrix. Furthermore, many of the potential functional groups may be modified post-translationally (e.g. by phosphorylation, acetylation, etc.) and therefore will not be accessible for the linking reaction.

Preferred reactions for conjugation of biologically active molecules and linkers include:

1) Amino-linkage, or formation of an amide bond between a linker and a ligand (e.g. protein) via reaction between ester function at the linker's end and the protein's primary and/or secondary amines. Such reactions are generally reliable and the activity of the immobilized protein is very rarely affected. Furthermore, the reaction can be performed at neutral pH (for primary amines) rising to around pH 8.3 (for secondary amines). Furthermore, the reaction requires no free amines in the reaction mixture.

2) Thio-linkage, or formation of a covalent bond between a thiol present on the matrix and another thiol originating from the protein. In this reaction, the conjugation reaction is reversible, i.e. the ligand can be removed back into fluid phase after reduction with 2-mercaptoethanol or DTT. This can be very convenient for studying interactions between proteins, for example. The reaction requires some special condition for conjugation, i.e. the absence of II-valent metals in the solution; and the protein must have SH-groups reduced prior to conjugation.

3) Carboxylic linkage, or formation of the covalent bond between the functional group on the matrix and carboxy-terminus of the protein. This type of reaction is less efficient and reliable because many proteins have C-termini which are naturally modified (i.e. blocked).

In one embodiment, a ligand which binds to a protein associated with chromatin is immobilized on the surface of the matrix. In this embodiment, post-sintering, the matrix is provided with a surface which is non-aminated or essentially non-aminated. In this method, after oxidation (and preferably immediately after oxidation), a spacer is generated in a reaction between a carboxyl function on the matrix and 6-aminohexanoic acid. This reaction produces a linker with the anchoring carboxylic function. Importantly, this approach does not involve generation of unbound amines on the surface, which significantly reduces the non-specific background binding to the modified surface.

The linker is preferably one which is long enough to prevent any steric hindrance between the support and the protein which binds to the ligand. Linkers may also be introduced to create a large enough distance between ligand attachment sites thus providing non-restricted access of the ligands to reagents and also preventing aggregation of the ligands on the surface of the polymer.

In conjugation of biologically active molecules, the length of the linker will determine the distance between the ligand and solid support. It has been shown that this length may significantly affect the functional activity of a biological molecule which is attached via the linker. Preferably, the linker will comprise from 3 to 11 carbon atoms, most preferably 3, 4, 5, 6, 7 or 8 carbon atoms. The linker may either be a cleavable linker or a non-cleavable linker. The term "cleavable linker" is intended to mean a linker that is cleavable under conditions which do not affect the activity of the ligand which is bound via the linker to the matrix.

The ligand which is attached to the matrix, optionally via a linker, may be any agent which binds to a protein associated with the chromatin. Typically the ligand is a protein, polypeptide, peptides, peptide mimetic, antibody or fragment thereof (e.g. monoclonal, polyclonal, Fab, scFv). Preferably the ligand comprises an agent which binds to an antibody, e.g. an anti-immunoglobulin (e.g. anti-IgG) antibody, protein A or protein G. Alternatively the ligand may comprise an antibody which binds to the protein of interest, e.g. the ligand may be an anti-histone antibody.

The matrix will in general be porous, i.e. pores or spaces will be present within the matrix through which liquids may pass. The matrix of the invention may take any convenient physical form, for example sheets, filters, membranes, cylinders, fibres or tubes. In one preferred embodiment, the matrix comprises a filter, disc or frit. The matrix typically functions as an adsorbent (i.e. by binding the protein associated with chromatin by virtue of the ligand on its surface). Thus whilst in some embodiments the matrix may be in the physical form of a filter (e.g. a disc or frit), the matrix need not function as a typical filter. In one embodiment, the matrix comprises an adsorbent disc or frit.

The matrix may be provided as a separate entity or it may form an integral part of another entity. For example, the matrix may be incorporated into separation devices such as columns, centrifuge vials, cartridges or syringes, and, depending on the sample and the downstream processes to be operated, one or more of such devices may be provided in a serial or parallel manner. Such devices may be handled manually, semi-automatically or in fully-automated fashion.

Separation Column

The rigid porous matrix may be contained within any type of vessel, provided that the arrangement permits a liquid sample to be passed through the matrix. Preferably the matrix is contained within a separation column.

In one embodiment, the separation column comprises a chamber for holding the liquid sample comprising chromatin, and an effluent port. Typically the effluent port is positioned at a lower end of the column. The column typically comprises an opening at an upper end of column through which a liquid sample can be added. In one embodiment, the rigid porous matrix is positioned above the effluent port, i.e. between the liquid sample in the chamber and the effluent port. In this embodiment the separation column is referred to as a gravity flow column.

In some embodiments, the column further comprises a hydrophobic matrix. The hydrophobic matrix typically does not comprise a bound ligand, but in other respects may be a rigid porous matrix as described above. For instance, the hydrophobic matrix may be formed from similar materials as the rigid porous matrix, e.g. sintered thermoplastic polymer particles. However the hydrophobic matrix typically has an unmodified or underivatized surface, e.g. the hydrophobic matrix lacks functional groups such as hydroxyl, carboxyl or amino groups. In some embodiments, the hydrophobic matrix may be formed from a thermoplastic polymer such as polyethylene, typically with an unmodified surface. The absence of hydrophilic functional groups typically renders the matrix sufficiently hydrophobic to perform its function, i.e. to retain the liquid sample within the column for a desired period. However, in alternative embodiments the hydrophobic matrix may be modified with a hydrophobic functional group such as e.g. a perfluoroalkyl group.

The hydrophobic matrix may be in the form of, for example, a filter, disc or frit. The hydrophobic matrix may be positioned between the rigid porous matrix and the effluent port of the column. The hydrophobic matrix may serve to retain the liquid sample within the column, i.e. to prevent leakage from the chamber in the column, until it is desired to flush the sample through the matrix and out of the column. In embodiments incorporating a hydrophobic frit or other means of preventing liquid flow by gravity the column is referred to as a spin column.

The separation column may be in any suitable form depending on the nature of the assay, and particularly the method used to draw the liquid through the matrix. Thus the separation may, for example, be a gravity flow column, vacuum column or spin column.

In one embodiment, the separation column is a micro-spin column, e.g. which fits a 1.5 or 2.0 ml micro-centrifuge tube suitable for use in a table-top microcentrifuge. Typically the column further comprises a collection vessel for receiving liquid which has passed through the rigid porous matrix and exited the column.

Figure 11:
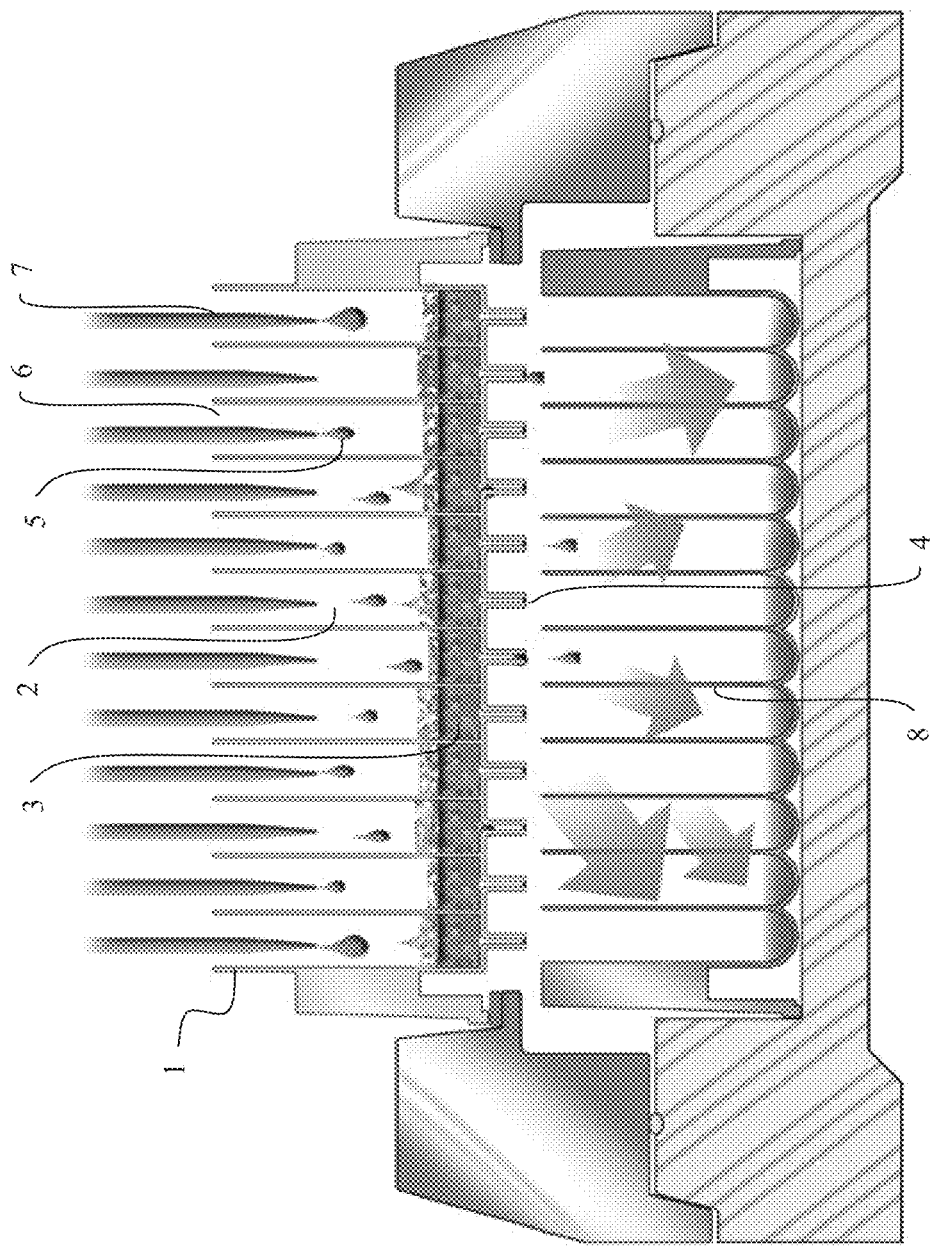
FIG. 11: High throughput processing format. A filtration microplate (1) comprising a plurality of wells (2) is shown, each well comprising a separation column according to the present invention. Each separation column comprises a rigid porous matrix in the form of a filter disc or fit (3) positioned above an effluent port (4) of the column. The rigid porous matrix has a ligand immobilized thereon which binds to a protein associated with chromatin. A liquid sample (5) is introduced into each well through an upper opening (6) using a multichannel pipette (7) and/or an automated (e.g. robotic) liquid handling system. The liquid sample may be drawn through each well of the filtration microplate by a vacuum, gravity or centrifugal force. The sample passes through the rigid porous matrix in each well of the filtration microplate, exits each well through an effluent port (4) and is received in a collection vessel (8) positioned below each well of the plate.

In one embodiment, an array comprising a plurality of separation columns according to the invention is provided. For instance, the separation columns may form part of a multiwell plate suitable for high throughput screening. In one embodiment a plurality of separation columns may be provided within a multiwell plate, e.g. a filtration microplate, each separation column corresponding to an individual well within the plate. Various multiwell plate formats are available and are compatible with multichannel pipettes and automated (e.g. robotic) liquid handling systems. For instance, in specific embodiments a 96, 384 or 1536 well format may be used, i.e. the multiwell plate comprises 96, 384 or 1536 separation columns. In one embodiment, a filtration microplate as shown in FIG. 11 may be used.

Passing a Liquid Sample Through the Matrix

Any suitable method may be used for passing the liquid sample through the matrix. In one embodiment the liquid sample is first added to a chamber in a separation column, e.g. through an upper opening in the column. The liquid sample may then pass through a rigid porous matrix, typically positioned above an effluent port at a lower end of the column, and thereby exit the column. In this way, chromatin fragments present in the liquid sample can bind to the ligand whilst passing through the matrix. Chromatin fragments are thereby separated from the liquid sample, which may then be discarded.

In embodiments of the present invention, the liquid sample may be drawn through the matrix in a centrifuge, by gravity or by a vacuum.

In some embodiments, the liquid sample is incubated with the matrix for a suitable period, e.g. after adding the sample to the column and before withdrawing the sample from the column. For example, the liquid sample may be incubated with the matrix for a period of 30 seconds to 48 hours, e.g. 1 minute to 12 hours, 1 minute to 2 hours, 5 to 60 minutes or about 30 minutes. The length of this incubation may be varied in order to allow sufficient time for the ligand to bind to the chromatin, depending on the kinetics of this reaction.

The volume of the liquid sample may vary depending on the volume of the chamber in the column and the dimensions of the matrix (e.g. frit). The matrix is porous, and typically may have a porosity of around 0.5, i.e. about 50% of the total volume of the matrix is internal void space. In one embodiment, the liquid sample is added in a volume such that it is completely absorbed by the matrix, i.e. the internal void space of the matrix is greater than or equal to the volume of the liquid sample. For example, a porous matrix suitable for use in a spin column may be in the form of a disc of diameter about 7.2 mm and thickness of about 2 mm. Such a matrix has a volume of about 80 µl and assuming a porosity of 0.5 the internal void volume would be around 40 µl. Thus the liquid sample could be added in a volume of about 40 µl. Where a hydrophobic matrix is used to retain the liquid sample in the column, preferably the matrix is hydrophobic enough to essentially prevent any liquid penetrating into the hydrophobic matrix.

Washing

After passing the liquid sample through the matrix, in one embodiment the column is washed to reduce non-specific binding to the matrix. One or more wash steps may be employed, typically by adding a wash solution to the column and passing the wash solution through the matrix.

For example, the matrix may be washed with a high stringency buffer to eliminate non-covalent interactions. A high stringency buffer may contain e.g. 20-50 mM Tris-HCl (pH 8.0), 1-5 mM EDTA, 0.1-0.5% SDS, 0.5-1M NaCl, and 0.5-1% TRITON X-100. Alternatively, the wash buffer may comprise PBS containing 0.5% of TWEEN-20, or 100 mM sodium phosphate containing 200 mM NaCl and detergents such as TWEEN-20 or TRITON X-100. Typically the washing step may involve a series of buffers with varying stringencies, e.g. a low stringency buffer comprising a relatively low salt concentration and a high stringency buffer having a higher salt concentration.

Preferably the wash buffer comprises at least 0.1% SDS, more preferably about 0.2% SDS. In one embodiment, the method comprises 1, 2 or 3 wash steps, preferably 3 wash steps. Preferably the wash buffer comprises NaCl, with LiCl being less preferred.

Reversal of Crosslinking

In embodiments where the sample comprised crosslinked DNA-protein complexes, the crosslinking can be reversed after washing. The buffer for crosslink reversal can be optimized to maximize reversal of the crosslinks and minimize DNA degradation resulting from chemical, biochemical and thermodynamic action.

For example, in one embodiment the buffer for reversal of crosslinking comprises EDTA, SDS, and proteinase K, which should efficiently degrade proteins complexed with DNA and prevent degradation of DNA by nucleases such as DNAse I. A further buffer may also be used comprising sodium and potassium salts with a high concentration, e.g. sodium chloride at 1M or potassium chloride at 0.5 M. Such buffers have been demonstrated to efficiently reduce DNA degradation from chemical and thermodynamic action (Marguet, E. Fortune, P, Extremophiles, 2: 115-122, 1998) and increase the reversing rate of formaldehyde crosslinks. Typically reversal of crosslinking takes place at elevated temperature, e.g. 50-85° C. for 5 min-4 hours, preferably at 65-75° C. for 0.5-1.5 h.

In some embodiments of the present invention, the reversal of crosslinking step may take place within the separation column. Alternatively, the rigid porous matrix (e.g. in the form of a filter or frit) may be removed from the separation column (e.g. before or after washing) such that reversal of crosslinking takes place in a different vessel. In further embodiments, the chromatin bound to the matrix may first be eluted from the column before reversal of crosslinking.

DNA Capture and Analysis

Once reversal of the crosslinked DNA-protein complex is completed, DNA may be captured and cleaned. This may be achieved by the standard technique of phenol-chloroform extraction, or by capturing DNA on a further solid phase (e.g. silica dioxide or nitrocellulose in the presence of high concentrations of non-chaotropic salts).

Following the purification step, the DNA fragments isolated may then be analysed, and their identity determined. This is preferably achieved by PCR. For example, the analysis step may comprise use of suitable primers, which during PCR, will result in the amplification of a length of nucleic acid. The skilled person will appreciate that the method may be applied to detect genes or any region of the genome for which specific PCR primers may be prepared. The PCR results may be viewed, for example, on an electrophoretic gel.

Applications

The present method may have a number of applications, including any of those for which ChIP assays are currently used, and may be applied to a wide variety of biological sample types. For instance, the method may be used in various research applications to characterize DNA/protein interactions. Variables such as histone protein modification, non-histone protein modification, and/or DNA methylation are key regulators of gene expression, and changes in them are associated with altered cell function or dysfunction, and hence disease. Since ChIP assays can be used to study variation in such epigenetic markers, the present method may be applied in diagnostic and prognostic applications and as a guide to appropriate treatment regimens.

Accordingly in one aspect the present method may be used for the diagnosis or prognosis of a disease condition. The method may be used, for example, in the diagnosis or prognosis of cancer, such as prostate, cervical cancer, or Hodgkin's lymphoma, and autoimmune diseases, such as rheumatoid arthritis. Preferably, the diagnostic method is carried out in vitro.

In one embodiment, the method may comprise taking first and second samples, and performing a ChIP assay according to the present method on each sample. For example, the first sample may comprise normal (a control) cells, and the second sample may comprise cells which are suspected to be diseased. By comparing the results of such an analysis, the method can be used to categorise a sample as being diseased or non-diseased.

Kits

Components for use in the present method may be provided in the form of a kit, optionally packaged with instructions for performing the method. Such kits may comprise, for example, a separation column as described above, and optionally one or more further reagents for performing a chromatin immunoprecipitation assay. Typical reagents for inclusion in the kit include one or more buffers or solutions for preparing the liquid sample, crosslinking chromatin, washing the matrix, reversal of crosslinks, and/or DNA purification.

The invention will now be described with reference to the following non-limiting examples.

EXAMPLES

Example 1

Chromatin Immunoprecipitation (ChIP) is an important technique in the study of DNA/protein interactions. The ChIP procedure however has limitations, it is lengthy, can be inconsistent and is also prone to non-specific binding of DNA and proteins to the bead based solid-phase matrices, which are often used for the immunoprecipitation step. In this example, we examined the utility of a new matrix, BioVyon™-Protein A, a solid support based on porous polyethylene, for ChIP assays. In ChIP experiments carried out using two antibodies and seven DNA loci, the performance of BioVyon™-Protein A was significantly better, with a greater percentage of DNA pull down in all the assays tested compared to bead based matrices, Protein A Sepharose® and Dynabeads® Protein A. Furthermore the rigid porous disc format within a column made the BioVyon matrix much easier to use with fewer steps and less equipment requirements, which resulted in a significant reduction in the time taken to process the ChIP samples. In summary, the BioVyon™-Protein A provides a column based assay method for ChIP and other immunoprecipitation based procedures; the rigid porous structure of BioVyon™ enables a fast and robust protocol without significant loss of product.

Introduction

The Chromatin Immunoprecipitation (ChIP) assay is an important research tool in modern molecular biology [1; 2; 3; 4; 5]. It allows the study and identification of DNA sequences which are specifically bound to particular proteins which are important regulatory elements in transcriptional machinery. The ChIP assay is a complex procedure, which includes several steps: DNA/protein crosslinking, sonication, immunoprecipitation (IP) of the crosslinked DNA/protein complexes, capture of these complexes and, finally, DNA recovery from the precipitated product and DNA analysis. During the IP step, antibodies specific to the protein component are employed, and capture of the immunoglobulin/DNA/protein complexes is achieved by the specific binding of immunoglobulins to Protein A and/or Protein G conjugated to a solid support [6]. DNA analysis can be carried out by PCR, Real Time PCR, hybridization on microarrays (ChIPChIP) [7; 8] or direct sequencing (ChIP-Seq) [9].

Figure 3A:
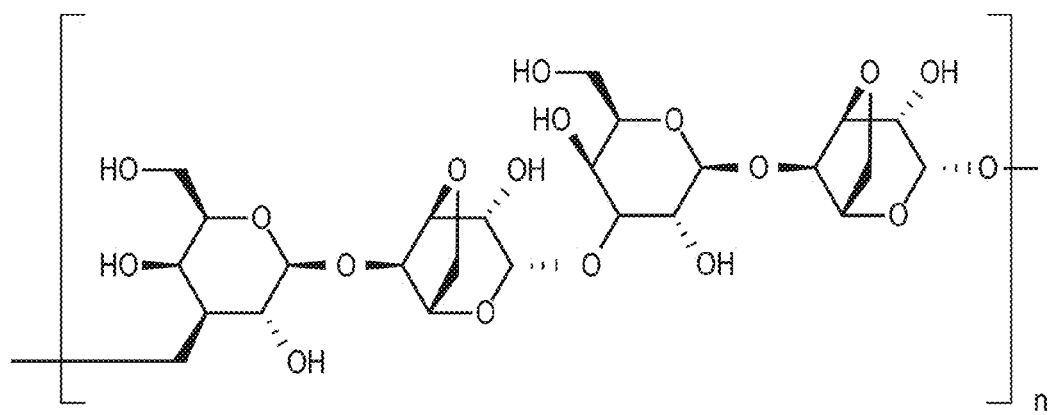
FIGS. 3A and 3B: Chemical structures of Sepharose® and BioVyon™. The Sepharose® dimer consists of Galactose and 3,6-Anhydro-L-galactose as shown in (FIG. 3A) whereas the BioVyon™ monomer is $C_2H_4$ as shown in (FIG. 3B).

ChIP assays however suffer from inherent problems, which can often lead to misleading, or even erroneous interpretation of the ChIP data [4]. These problems arise during IP, the most crucial part in the ChIP assay. Two main components of IP determine the quality and quantity of the ChIP DNA, the antibody and the solid support used for binding the antigen/antibody complex. Antibodies contribute to non-specific binding and may be responsible for a low yield of the recovered DNA due to a low affinity for the protein bound to the DNA. However, the bulk of non-specific binding to the solid support, in particular to agarose-based matrices such as Protein A Sepharose® beads commonly used in IP and ChIP assays, is thought to be due to the DNA/protein complexes reacting with diverse chemical groups on the surface of the Sepharose. Sepharose is derived from a naturally occurring material (seaweed) and has a very chemically heterogeneous base structure with a very high surface area (see FIG. 3A).

The high surface area of the Protein A variant has proved very useful for IP involving proteins, but tends to allow high levels of non-specific binding to the DNA in the chromatin targets of a ChIP assay, which can occur as a result of ionic interactions between the differently charged surfaces of sepharose and DNA. To minimize this problem, an additional DNA preblocking step is often recommended in ChIP protocols. During this step the sepharose-based solid support is pre-incubated with non-homologous DNA/RNA prior to IP to block any potentially active binding sites.

Figure 3B:
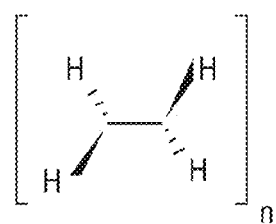

In this example we used an alternative matrix, BioVyon™-Protein A, available from Porvair Filtration Group Ltd, Fareham, UK, which is based on porous High Density Polyethylene (HDPE). BioVyon™ may be produced using methods as described in WO 2005/018803. BioVyon™ has very different polymer chemistry to sepharose; it is a synthetic polymer made up of repeat units of the hydrocarbon ethylene and is chemically homogeneous (see FIG. 3B), this structure is less variable and much more inert. The surface of BioVyon™ has been chemically etched by oxidation, which provides a moderate increase in surface area and allows the covalent attachment of a linker and a Protein A molecule (see FIGS. 4 and 5). The etching/oxidation process introduces a relatively low surface concentration of oxidized species (relative to a polysaccharide) leaving an inert surface with a concentration of Protein A sufficient for the ChIP assay. The chemical structure of the BioVyon™-Protein A, described above, is expected to exhibit reduced amounts of non-specific binding to DNA/protein complexes. In addition this difference in base chemical structure may also contribute to improved chemical stability of the BioVyon™-Protein A (compared to Protein A Sepharose®) during acid hydrolysis and oxidation processes that could occur during the ChIP assay.

Figure 6A:
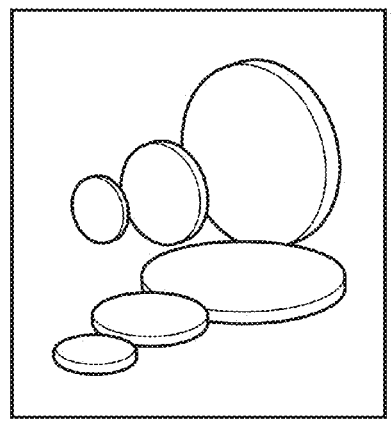
FIGS. 6A-6C: The BioVyon™ formats FIG. 6A. Rigid BioVyon™ discs with different diameters.
Figure 6C:
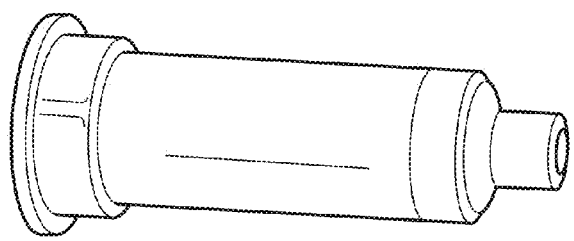
Figure 6B:
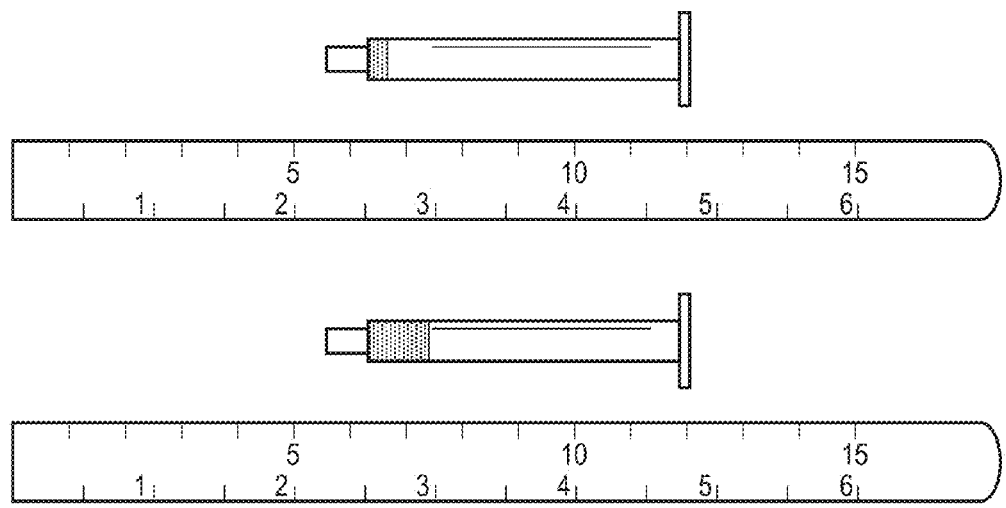

BioVyon™ is manufactured in the form of a solid but porous disc, which is rigid and incompressible, and inserted in a column (see FIGS. 6A-6C). This makes the BioVyon™ matrix easier to handle, than bead based matrices, and allows a column to be prepared with a precise amount of Protein A fixed at the base. No gel re-suspension is necessary and the BioVyon™ bed cannot be disrupted during the addition of reagents and buffers, in addition the errors involved in bead aspiration into a vessel are also removed.

In this example we carried out ChIP assays with two different antibodies and several DNA loci, using BioVyon™-Protein A in gravity flow columns. These results were compared with the results of ChIP assays obtained using other matrices under similar conditions (Protein A Sepharose® and Dynabeads® Protein A). Dynabeads® are superparamagnetic particles, coated with a polyacrylate polymer layer. From these experiments we concluded that the BioVyon™-Protein A matrix presents an attractive alternative to the existing matrices in ChIP and, potentially, in other IP based assays.

Materials and Methods

Cells NIH 3T3 mouse fibroblasts were maintained in DMEM (Lonza, Basel, Switzerland) supplemented with 10% donor serum and 50 µg/ml gentamicin (both from Invitrogen, San Diego, USA). MCF7, human breast cancer cells, were cultured in RPMI-1640 with Ultraglutamine 1 (both from Lonza, Basel, Switzerland), supplemented with 10% FBS (Biosera, East Sussex, UK) and 50 µg/ml gentamicin.

Lysates from NIH 3T3 cells for ChIP assays were prepared as follows. Approximately $5 \times 10^6$ cells were grown in a 75 cm$^2$ flask in 20 ml of DMEM culture medium. Cells were treated with formaldehyde added to the culture medium to a 1% final concentration for 10 min at 37° C., to cross-link the DNA/protein complexes. NH$_4$OH was then added to the medium to 0.5% final concentration for 5 min at room temperature (RT) to neutralize formaldehyde. Cold PBSM (Standard PBS buffer+2 mM MgCl$_2$) was then added, cells harvested, collected by centrifugation, and washed twice with cold PBSM.

Cells were then lysed in PBSM, 0.5% TRITON X-100, placed on ice for 15 min, nuclei collected by centrifugation at 6000 g for 10 min. The pellet was washed with cold PBSM, centrifuged and resuspended in NLB (10 mM Tris/Hepes pH8.0, 1 mM EDTA, 2.5 M NaCl, 0.5 mM PMSF) and incubated for 20 min on ice in NLB (1:5 v/v pellet/NLB). The suspension was layered onto the NLB+1M sucrose cushion at the following ratio: suspension/NLB+1M sucrose at 1/10 v/v and centrifuged for 10 min at 10000 g. The pellet was resuspended in the Low salt buffer, LS, (10 mM Tris/Hepes pH8.0, 1 mM EDTA, 150 mM NaCl) and sonicated at 5×1 min bursts with 1 min break on ice, power 3 using Bioruptor™ (Wolf Laboratories Limited, Pocklington, York, UK) until the desired lengths of DNA fragments were achieved (400-500 bp). Protease inhibitors were then added to the lysates at the following concentrations: Aprotinin 800 nM, Bestatin 50 µM, Leupeptin 20 µM, Pepstatin 10 µM, AEBSF 1 mM, E64 15 µM (Cat number: 78425 Thermo Scientific). If lysates were stored at −80° C., the protease inhibitors were added to the thawed lysates.

Lysates from MCF7 cells were prepared as follows. Approximately $5 \times 10^6$ cells were grown in a 75 cm$^2$ flask in 20 ml of RPMI culture medium. The medium was drained off and 1 ml of warm PBS was added to the cells. To cross-link the DNA/protein complexes, the cells were treated with 1% of formaldehyde (final concentration) for 10 min at RT shaking on a rotating platform. The reaction was quenched with 0.67M of glycine (final volume) for 5 min at RT with shaking.

Cells were then harvested and centrifuged at 3500 rpm for 5 min. The cell pellet was re-suspended in 2 ml of hypotonic buffer (10 mM Tris/HCl, pH 7.2, 2 mM MgCl$_2$, 0.5% TRITON X-100) and left on ice for 10 min. The nuclei were collected after the centrifuging at 5000 rpm for 5 min at 4° C. The pellet was re-suspended in 600 µl of Lysis Buffer (50 mM Tris/HCl pH8.0, 10 mM EDTA, 1% SDS), left on ice for 10 min and sonicated at 15×1 min bursts with 1 min break on ice, power 3 using Bioruptor™ (Wolf Laboratories Limited, Pocklington, York, UK) until the desired lengths of DNA fragments were achieved (400-500 bp). The samples were centrifuged for 10 min at 13,000 rpm at 4° C. The sonicated cell suspension was diluted 10 fold in the Upstate "ChIP dilution buffer" (0.01% SDS, 1.1% TRITON X-100, 1.2 mM EDTA, 16.7 mM Tris/HCl, pH 8.0, 167 mM NaCl). Protease inhibitors were then added to the lysates at following concentrations: Aprotinin 800 nM, Bestatin 50 µM, Leupeptin 20 µM, Pepstatin 10 µM, AEBSF 1 mM, E64 15 µM (Cat number: 78425 Thermo Scientific). If lysates were stored at −80° C., the protease inhibitors were added to the thawed lysates.

Antibodies for this study were as follows: anti-RNA Polymerase II (anti-Pol II) (8WG16) mouse monoclonal (Covance Research Products, Princeton, N.J., USA), previously used in ChIP assays [10]; anti-CTCF rabbit polyclonal (Upstate-Millipore, Massachusetts, USA), employed for genome wide ChIP analyses [e.g. [11; 12]]; anti-His-tag rabbit polyclonal (Abcam plc, Cambridge, UK); anti-β-actin mouse monoclonal (Sigma-Aldrich, St Louis, USA); mouse and rabbit IgG (Santa Cruz Biotechnology, Santa Cruz, Calif.).

Figure 4:
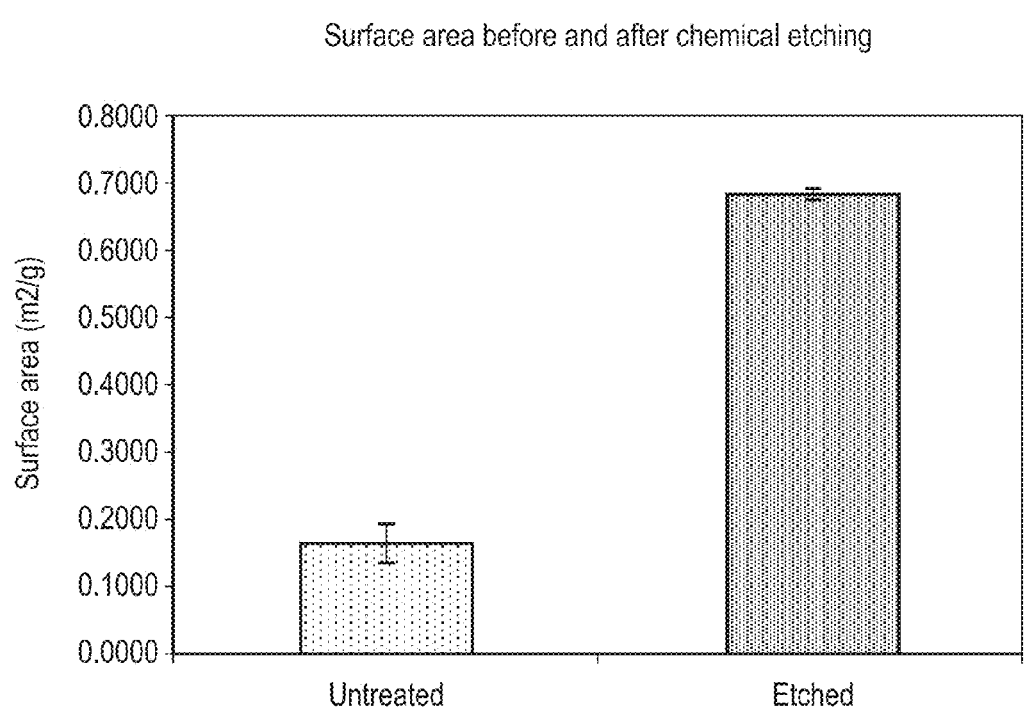
FIG. 4: Nitrogen adsorption analysis of surface area before and after chemical etching. Nitrogen adsorption analysis (BET method) was used to determine the surface area of the BioVyon™. This was done by determining the mass of nitrogen molecules adsorbed onto the surface at specific temperatures and pressures using a Gemini III 2375 surface area analyser (Micromeritics, Norcross, Ga., USA). A comparison of surface area for untreated and chemically etched BioVyon™ using nitrogen adsorption analysis (n=3) is shown.
Figure 5A:
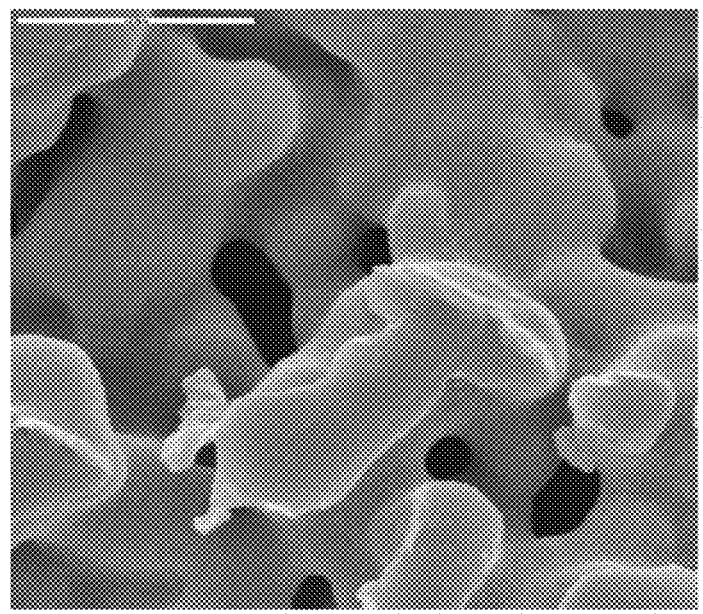
FIGS. 5A and 5B: Scanning electron microscope (SEM) photographs of BioVyon™ media Two samples of sintered BioVyon™ were subjected to scanning electron microscopy using a Hitachi S-520 Scanning Electron Microscope (Hitachi High Technologies Corporation, Tokyo, Japan).
Figure 5B:
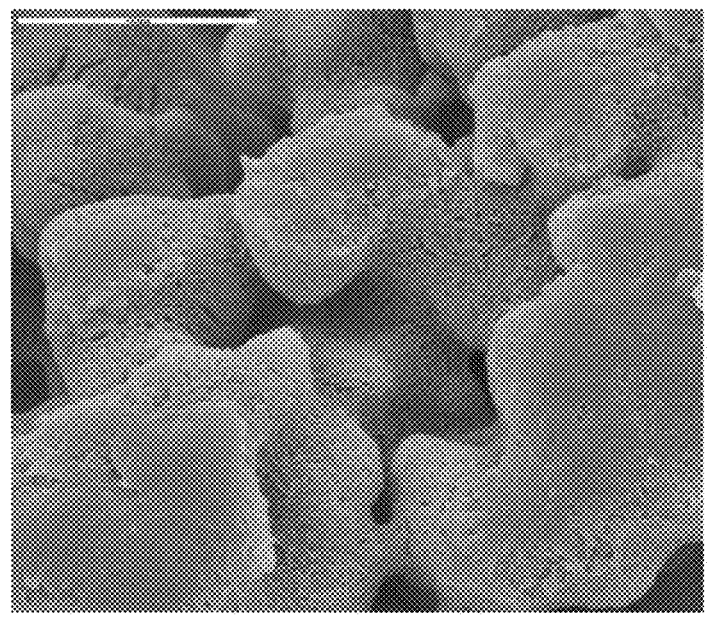

BioVyon™-Protein A gravity flow columns were obtained from Porvair Filtration Group Ltd, Fareham, UK. The columns have the same dimensions as a standard 1 ml Solid Phase Extraction (SPE) tube and contain a rigid porous HDPE BioVyon™-Protein A frit approximately 6 mm in diameter by 2 mm long (see FIG. 6B). The frits have been chemically treated to increase surface area using a selective oxidation method, which preferentially etched the surface and provided carboxylic acid anchor groups, for further covalent attachment. The pits caused by the etching process can be clearly seen in FIG. 5B, which compared the microstructure of the surface before and after etching. The pitting was responsible for the increased surface area as shown in FIG. 4. The surface has been tailored by this process to provide sufficient functionality for the immunoprecipitation stage of the ChIP assay. The anchor groups formed on the surface of the HDPE were then covalently coupled to the protein A via a linker to form the BioVyon™-Protein A solid-phase.

Chromatin immunoprecipitation (ChIP) assays were conducted according to the manufacturer's manual for the ChIP kit (Upstate-Millipore, Massachusetts, USA) for Protein A Sepharose® (Sigma-Aldrich, St Louis, USA), with some modifications. In ChIP experiments involving BioVyon™-Protein A, the above protocol, with some modifications, was applied; the Protein A Sepharose® slurry there was replaced by the BioVyon™—Protein A gravity flow columns. In the ChIP assays with Dynabeads® Protein A (Invitrogen, San Diego, USA) we followed the manufacturer's protocol. The detailed protocols of the ChIP experiments with the three different matrices are as follows.

Chromatin Immunoprecipitation (ChIP) Assays with Protein A Sepharose®

Chromatin immunoprecipitation (ChIP) assays with Protein A Sepharose® were performed using the ChIP kit (Upstate) according to the manufacturer's instructions with some modifications (cited from the Upstate ChIP kit manual). For ChIP assays using lysates from mouse NIH 3T3 cells, the following antibodies were used (4 μg of each per 500 μl of lysates): anti-Pol II, non-specific mouse IgG and anti-actin mouse monoclonal antibody. For ChIP assays using lysates from human MCF7 cells the following antibodies were used (100 μg of each per 500 μl of lysates): anti-CTCF, nonspecific rabbit IgG and anti-His-tag rabbit polyclonal.

1. For each reaction use 500 μl of diluted sonicated cell suspension.
2. Save 1% of the diluted cell suspension for INPUT.
3. Pre-clear the suspension by adding 80 μl of Salmon Sperm DNA/Protein A Sepharose-50% Slurry (SIGMA) for 30 min with agitation at 4° C.
4. Preblock the Protein A Sepharose® (0.2 ml) with 1 ml of the preblocking solution containing "Low salt" LS Buffer (0.1% SDS, 1% TRITONX-100, 2 mM EDTA, 20 mM Tris-HCl, pH 8, 150 mM NaCl)+1 mg/ml BSA+400 μg salmon sperm DNA. Mix Protein A Sepharose® with the preblocking solution and incubate with rotation for 30 min at 4° C. Spin at 500 rpm and remove supernatant.
5. Pellet beads by brief centrifugation (1100 rpm, 5 min, 4° C.) and collect the supernatant fraction.
6. Add immunoprecipitating antibody to the lysate and incubate with rotation at 4° C. for 3 hours.
7. Add 60 μl of Sperm DNA/Protein A Sepharose-50% Slurry for 1 h with rotation at 4° C. to collect the antibody/CTCF complex.
8. Pellet agarose by centrifugation (1000 rpm for 1 min at 4° C.).
9. Wash the complexes taking care for 3-5 min on rotating platform with 1 ml of the following buffers: LS, "Low salt" (0.1% SDS, 1% TRITONX-100, 2 mM EDTA, 20 mM Tris-HCl (pH 8), 150 mM NaCl), HS, "High salt" (0.1% SDS, 1% TRITONX-100, 2 mM EDTA, 20 mM Tris-HCl (pH 8), 500 mM NaCl), twice with "Final wash" (0.1% SDS, 1.1% TRITON X-100, 1.2 mM EDTA, 16.7 mM Tris-HCl, pH 8.0, 167 mM NaCl) ×2 and finally once with TE.

Elution and Extraction of DNA

1. Add 200 μl of the freshly prepared "Elution buffer" (1% SDS, 0.1M NaHCO3).
2. Incubate at 65° C. for 10 min. Vortex briefly. Spin down the sepharose beads at max speed for 5 min and carefully transfer the supernatant fraction (eluate) to another tube. Repeat this step twice.
3. Add 18 μl of 5M NaCl to the combined eluates (400 μl) and heat the eppendorf tubes at 65° C. for 4-5 h to reverse crosslinking.
4. Add 10 μl of 0.5M EDTA, 20 μl 1M Tris/HCl, pH 6.5 (6.8) and 1.5 μl of 14-22 mg/ml Proteinase K to the eluates and incubate for 1 h at 45° C.
5. Recover DNA by adding phenol/chloroform.
6. Re-suspend the pellet in 40 μl of $H_2O$.

Chromatin Immunoprecipitation (ChIP) Assays with Dynabeads® Protein A

Chromatin immunoprecipitation (ChIP) assays with Dynabeads® Protein A were conducted according to the manufacturer's (Invitrogen) manual with some modifications (cited from the Dynabeads® Protein A Invitrogen manual). For ChIP assays using lysates from mouse NIH 3T3 cells, the following antibodies were used (4 μg of each per 500 μl of lysates): anti-Pol II, nonspecific mouse IgG and anti-actin mouse monoclonal antibody. For ChIP assays using lysates from human MCF7 cells the following antibodies were used (100 μg of each per 500 μl of lysates): anti-CTCF, non-specific rabbit IgG and anti-His-tag rabbit polyclonal.

The steps were as follows:

1.1 Preparation of Dynabeads
1. Completely resuspend Dynabeads by pipetting or by rotating on a roller (5 minutes).
2. Transfer 50 μl (1.5 mg) Dynabeads to a test tube.
3. Separate on the magnet until the supernatant is clear and remove the supernatant.
4. Remove the tube from the magnet.
5. Proceed directly to Antibody (Ab)-binding (section 1.2)

1.2 Binding of Antibody (Ab)
6. Add your antibody diluted in 200 μl Ab *Binding & *Washing Buffer, to the tube from step 4 above.
7. Incubate with rotation for 10 minutes at room temperature.
8. Place the tube on the magnet and remove the supernatant.
9. Remove the tube from the magnet and wash by gentle pipetting to resuspend the beads in 200 μl Ab Binding & Washing Buffer.
10. Proceed directly to immunoprecipitation (section 2.3).

1.3 Immunoprecipitation of Target Antigen
11. Place the tube (from step 10) on the magnet and remove the supernatant.
12. Add your sample containing the antigen (Ag) (typically 100-1,000 μl) and gently pipette to resuspend the Dynabeads-Ab complex.
13. Incubate with rotation for 10 minutes at room temperature to allow Ag to bind to the Dynabeads-Ab complex. Note: Depending on the affinity of the antibody, it may be necessary to increase incubation times for optimal binding.
14. Place the tube on the magnet. Transfer the supernatant to a clean tube for further analysis, if desired.
15. Wash the Dynabeads-Ab-Ag complex three times using 200 μl Washing Buffer for each wash. Separate on the magnet between each wash, remove supernatant and resuspend by gentle pipetting.

16. Resuspend the Dynabeads-Ab-Ag complex in 100 µl Washing Buffer and transfer the bead suspension to a clean tube. This is recommended to avoid co-elution of proteins bound to the tube wall.

17. Place the tube on the magnet, remove the supernatant and proceed to elution and extraction of DNA as described in the protocol for Protein A Sepharose® (see above).

Buffer Composition:
Binding buffer: PBS/TWEEN 20 (1×PBS pH 7.4./0.02% TWEEN 20)
Washing buffer: PBS Optimized Protocol for Chromatin Immunoprecipitation (ChIP) Assays with BioVyon™-Protein A Gravity Flow Columns The immunoprecipitating antibodies were added to the lysate and incubated with rotating at +4° C. for 3 hours. For ChIP assays using lysates from mouse NIH 3T3 cells, the following antibodies were used (4 µg of each per 500 µl of lysates): anti-Pol II, non-specific mouse IgG and anti-actin mouse monoclonal antibody. For ChIP assays using lysates from human MCF7 cells the following antibodies were used (100 µg of each per 500 µl of lysates): anti-CTCF, non-specific rabbit IgG and anti-His-tag rabbit polyclonal.

The BioVyon™-Protein A gravity flow columns were prepared as follows (all manipulations with the columns were at RT by gravity flow): columns were first washed with distilled water, then three times with 1 ml of ChIP Dilution buffer (0.01% SDS, 1.1% TRITON X100, 1.2 mM EDTA, 16.7 mM Tris/HCl, pH8.0, 167 mM NaCl). Cell lysate was then applied onto the column and washing steps were performed: three washes with 1 ml of LS buffer (Low Salt Buffer: 10 mM Tris/Hepes pH8.0, 1 mM EDTA, 150 mM NaCl), three washes with 1 ml of MS buffer (Medium salt buffer: 0.1% SDS, 20 mM Tris/HCl pH8.0, 2 mM EDTA, 150 mM NaCl, 1% TRITON X100) and three washes with 1 ml of HS buffer (High salt buffer, 0.1% SDS, 20 mM Tris/HCl pH8.0, 2 mM EDTA, 500 mM NaCl, 1% TRITON X100). DNA was eluted with 500 µl of the Elution buffer (7M urea, 50 mM 2-ME), then NaHCO$_3$ and NaCl were added to final concentrations of 0.1M and 0.5M respectively and the eppendorf tubes were heated at 65° C. for 4-5 hrs to reverse cross-linking. After this step, 25 µl of 0.5M EDTA, 50 µl 1M Tris/HCl, pH 6.5 and 1.5 µl of 14-22 mg/ml Proteinase K were added to the eluates and tubes were incubated for 1 hr at 45° C. The DNA was then extracted with phenol/chloroform, the aqueous phase recovered and precipitated with two-three volumes of ethanol; 20 ng of glycogen (carrier) was added to the solution. It was then centrifuged at 10,000 rpm for 10 min and the DNA pellet resuspended in 40 µl of H$_2$O.

Real Time PCR (Q-PCR) and PCR reactions The primers and conditions for PCR and Q-PCR are described in Table 1. Real-time PCR reactions were performed as reported earlier with modifications [13]. In brief, the reaction components were assembled in a 25 µl mixture containing 3 µl of sample, 200 nM of each primer and 12.5 µl of SensiMix Plus SYBR Green PCR kit (Quantace, London, UK). Amplification, data acquisition and analysis were conducted using the Chromo4 Real Time PCR (BioRad Laboratories, California, USA). Dissociations curve analysis was performed for each sample after PCR reaction to verify that a single amplicon of the expected melt-curve characteristics was obtained. The amount of precipitated DNA was calculated relative to the total input chromatin and expressed as a percentage of the total, according to the formula: % Input=$2^{\Delta Ct} \times 100\%$, where $\Delta Ct=Ct$ (input)−Ct (immunoprecipitation), and Ct is the mean threshold cycle of the corresponding PCR reaction. These experiments were carried out in triplicate and the average was obtained from the % Input.

TABLE 1

Primers and conditions for PCR and real-time PCR analyses used in ChIP assays.

| Primers | Ref. | Forward primer (5'-3' direction) | Reverse primer (5'-3' direction) | PCR Fragment Size (bp) | PCR conditions (for all-initial denaturation: 94° C. 5 min; final elongation- 72° C. 10 min) | Real-Time PCR conditions (for all-initial denaturation: 95° C. 10 min; final elongation- 72° C. 5 sec) |
|---|---|---|---|---|---|---|
| GAPDH (promoter, TATA-box) mouse | [1] | tcctgcaatg atagactag | ctgccaaaca cgttcacaga | 158 | Cycle(x30): 95° C. 30 sec; 55° C. 30 sec; 72° C. 20 sec. | Cycle(x40): 95° C. 15 sec; 58° C. 30 sec; 72° C. 20 sec. |
| N-site- Myc human | [1; 2] | acctgacccc cgccctcgtt ga | ctctactggc agcagagatc at | 58 | Cycle(x30): 95° C. 30 sec; 65° C. 30 sec; 72° C. 20 sec | Cycle(x40): 95° C. 15 sec; 58° C. 30 sec; 72° C. 20 sec |
| β-Globin human (5'HS5) | [3] | ttgggtttga atcgatacgc | gcacccacct tcaatcaaaa | 155 | Cycle(x30): 95° C. 30 sec; 55° C. 30 sec; 72° C. 30 sec | Cycle(x40): 95° C. 15 sec; 55° C. 30 sec; 72° C. 30 sec |
| DM1 Human (CTCF site 1) | [4] | gcctgccagt tcacaacc | cattcccggc tacaaggac | 145 | Cycle(x30): 95° C. 30 sec; 60° C. 30 sec; 72° C. 30 sec | Cycle(x40): 95° C. 15 sec; 58° C. 30 sec; 72° C. 30 sec |
| H19 ICR (CTCF site 1) Human | [5; 6] | cccatcttgc tgacctcac | agacctggga cgtttctgtg | 165 | Cycle(x30): 95° C. 30 sec; 60° C. 30 sec; 72° C. 30 sec | Cycle(x40): 95° C. 15 sec; 58° C. 30 sec; 72° C. 30 sec |

TABLE 1-continued

Primers and conditions for PCR and
real-time PCR analyses used in ChIP assays.

| Primers | Ref. | Forward primer (5'-3' direction) | Reverse primer (5'-3' direction) | PCR Fragment Size (bp) | PCR conditions (for all-initial denaturation: 94° C. 5 min; final elongation- 72° C. 10 min) | Real-Time PCR conditions (for all-initial denaturation: 95° C. 10 min; final elongation- 72° C. 5 sec) |
|---|---|---|---|---|---|---|
| PLK Human | [7] | ttgcctttgc ggttctaaca | ggaattcctt cggggtact | 161 | Cycle(x30): 95° C. 30 sec; 55° C. 30 sec; 72° C. 30 sec | Cycle(x40): 95° C. 15 sec; 55° C. 30 sec; 72° C. 30 sec |
| PIM Human | [7] | ttgggtttga atcgatacgc | ctctcgcggt cagaatgg | 160 | Cycle(x30): 95° C. 30 sec; 60° C. 30 sec; 72° C. 30 sec | Cycle(x40): 95° C. 15 sec; 58° C. 30 sec; 72° C. 30 sec |

Statistical analysis Statistical analysis was carried out using unpaired Student's t test. A significant value was detected when the probability was below the 5% confidence level (P<0.05).

Results and Discussion

In the ChIP protocol developed for BioVyon™-Protein A, the IP step required optimization for use with this solid support. As a model test system for ChIP in this study, we chose a previously described assay for detection of binding of RNA Polymerase II to a TATA-box within the promoter region of the mouse GAPDH gene [10; 14].

Pre-blocking of Sepharose beads in routine ChIP helps to prevent non-specific binding of DNA/protein complexes to Sepharose during the IP step. This was confirmed in our tests, whereby the omission of the pre-blocking step led to higher background with both, Protein A-Sepharose beads and Dynabeads® Protein A (FIG. 1). For the BioVyon™—Protein A columns, the pre-blocking step actually slightly increased the non-specific binding (FIG. 1) and therefore was excluded from the ChIP protocol.

Figure 7A:
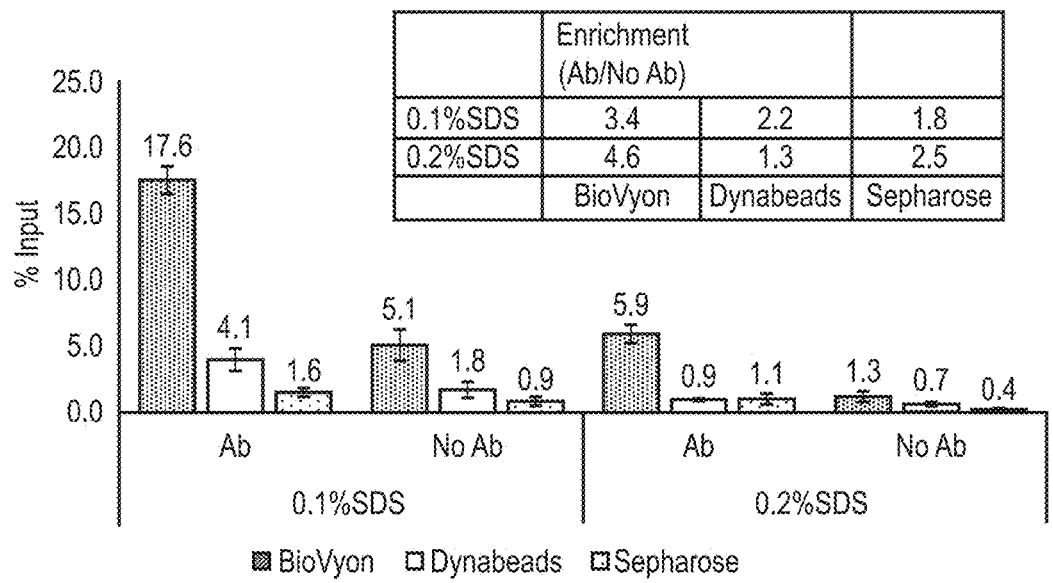
FIGS. 7A and 7B: Real-time PCR analysis of PCR products from optimization experiments for the washing steps and detergent concentration for ChIP assays using BioVyon™-Protein A (in gravity flow columns). ChIP assays with the mouse monoclonal antibodies against RNA Polymerase II were performed using crosslinked cell lysates obtained from NIH 3T3 mouse fibroblasts. The DNA recovered after ChIP procedures was PCR amplified with primers overlapping the GAPDH TATA-box (see Table 1). Three separate experiments were conducted, and quantification of three replicates of a typical experiment is shown. Ab=Antibody present, No Ab=No Antibody present. The enrichment values represent the ratio of the RT-PCR value of a ChIP assay with the antibody to the corresponding control (ChIP assay without the antibody).

We then explored whether the low non-specific binding to BioVyon™-Protein A columns could be further reduced by changes to wash buffer formulation and number of washes. Introduction of sub-denaturing amounts of ionic detergent such as SDS is known to improve the signal/background (Antibody/No Antibody) ratio in ChIP experiments with Protein A Sepharose®. To compare how an increased concentration of SDS affects signal/background ratio on Protein A Sepharose®, Dynabeads® Protein A and BioVyon™—Protein A, washing solutions with two different concentrations of SDS (0.1% and 0.2%) were tested using the protocol which included the pre-blocking step for all matrices. At a higher concentration of SDS (0.2%), the signal/background ratio for Protein A Sepharose® and BioVyon™-Protein A increased, whereas it decreased considerably for Dynabeads® Protein A (FIG. 7A).

Figure 7B:
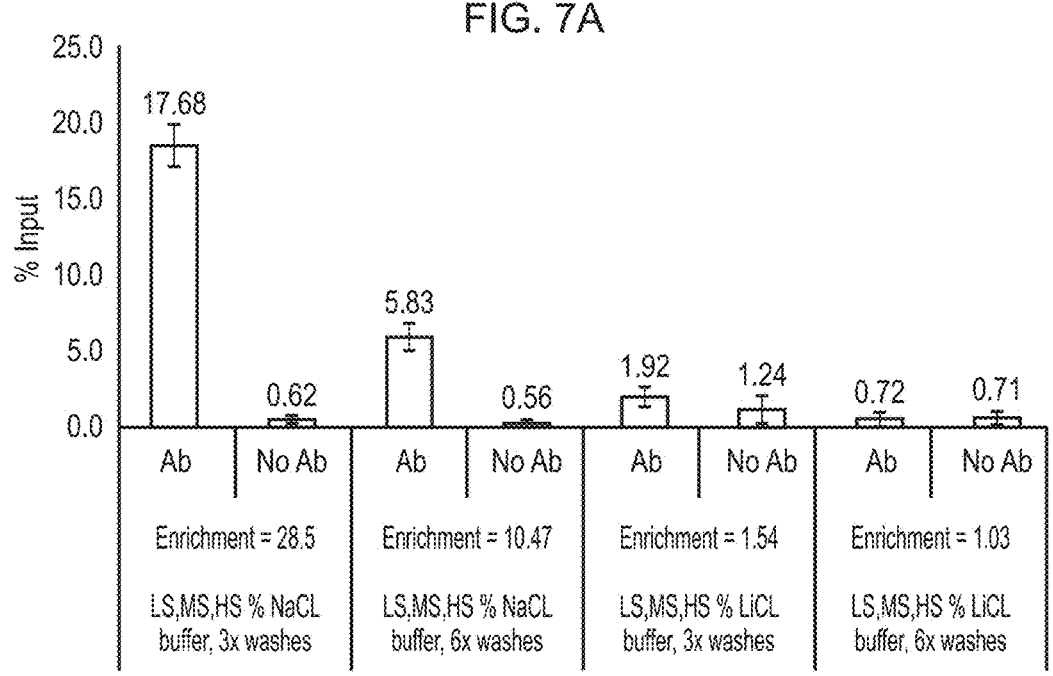

We also studied the effects of washing intensity on the quality of ChIP assays. In these experiments, after binding of DNA/protein complexes, the columns were washed either three or six times with buffers of different chemistries. As shown in FIG. 7B, three washes were optimal; six washes considerably reduced the specific signal.

It was previously empirically observed that non-specific binding of nucleic acids to Protein A Sepharose beads can be decreased by using LiCl instead of NaCl in the buffer and this is why LiCl is included in many ChIP protocols. However, this step in ChIP assays using BioVyon™—Protein A columns did not decrease the non-specific background binding; moreover, it caused a significant reduction of the specific signal (FIG. 7B).

The series of tests performed with various buffer compositions resulted in an optimized protocol for the BioVyon™-Protein A, which differed from the Upstate protocol in that (i) it did not include a pre-blocking step and (ii) optimal washing conditions were three washes with the LS, MS, HS buffers (0.1% SDS was used during the washing step with HS) and the LiCl buffer was omitted from the procedure in favour of a NaCl buffer.

We hypothesized that different effects of blocking, LiCl and SDS on BioVyon™—Protein A, Protein A Sepharose® and Dynabeads® Protein A may be explained by differences in chemical properties of the matrices, whereby more non-specific DNA binding is likely to occur with Protein A Sepharose® and Dynabeads® Protein A than with Bio-Vyon™—Protein A.

Figure 2A:
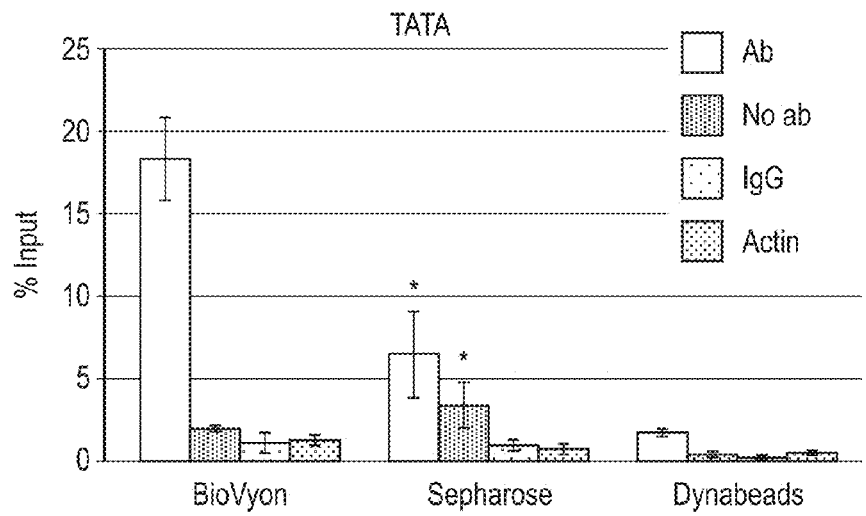
FIGS. 2A and 2B Real-time PCR analysis showing comparison of BioVyon™—Protein A (in gravity flow columns), Protein A Sepharose® and Dynabeads® Protein A in ChIP assays. Real-Time PCR analysis of ChIP DNA was performed as described in Example 1. In the experiments involving Protein A Sepharose® the Upstate protocol was used, for Dynabeads® Protein A we followed the manufacturer's protocol and for BioVyon™-Protein A an optimized ChIP protocol was used. Three separate experiments were conducted, and quantification of three replicates of a typical experiment is shown. Error bars indicate Standard Deviations. The differences in the enrichment in the ChIP DNA with the specific antibody between BioVyon™-Protein A and the controls were statistically significant in all experiments ($P<0.05$), except the enrichment to no antibody (indicated by asterisks). Abbreviations: "Ab"—anti-RNA Polymerase II antibody for FIG. 2A and anti-CTCF rabbit polyclonal antibody for FIG. 2B; "No ab"—no antibody; IgG-nonspecific mouse IgG, "Actin"—anti-actin mouse monoclonal (irrelevant) antibody, "Histag"—anti-His-tag rabbit polyclonal (irrelevant) antibody.

BioVyon™-Protein A, Protein A Sepharose® and Dynabeads® Protein A were then used in parallel in ChIP assays with the same specific antibody and the DNA locus as described above (FIG. 1) and also controls for non-specific DNA binding were included. In these experiments, the differences in the enrichment in the ChIP DNA with the specific antibody between BioVyon™-Protein A, controls and the other two matrices were statistically significant (P<0.05) (FIG. 2A). The DNA pull down (% input) was significantly higher for the BioVyon™-Protein A than for the other matrices in these assays.

Figure 2B:
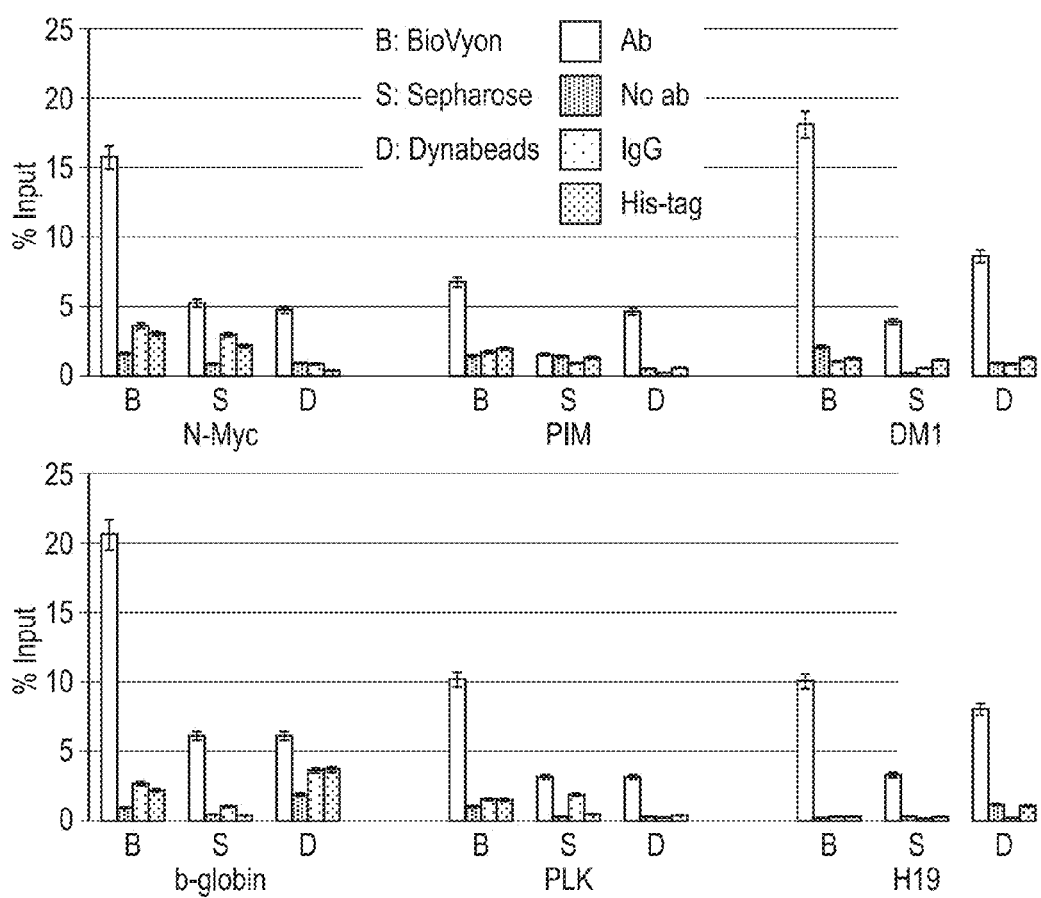

We extended these tests to include another antibody and several DNA loci. From this perspective a transcription factor, CTCF [15; 16; 17], is an ideal candidate since it has numerous binding sites in the genome [11; 18], many of them are characterized [15] and our laboratory specializes on studies of CTCF. The CTCF binding (target) sites (CTSs) represent good experimental models to test in ChIP assays since they differ in their affinity to CTCF. We selected the following six human CTSs: N-site Myc [10; 19], PIM [15], DM1 [20], β-globin [21], PLK[15] and H19 [22; 23]. The DNA pull down (% input) was higher for the BioVyon™-Protein A than for the other matrices for all 6 loci. The ChIP DNA enrichment with BioVyon™-Protein A did vary between the CTSs, which most likely reflected the affinity of different CTSs to CTCF (FIG. 2B). The enrichment in the ChIP DNA with the specific antibody between BioVyon™-Protein A and all the controls were statistically significant ($P<0.05$).

It should be noted that the values of non-specific controls for different DNA loci varied considerably. In some cases more non-specific product was obtained with no antibody than with IgG and irrelevant antibodies. Such patterns however are not unusual and were previously reported in the literature (for examples see references [24; 25]). It is possible that the combination of particular features of a DNA binding site (e.g. base composition, length of an amplicon etc), together with particular properties of a matrix, might contribute to these differences. The practical recommendation from these experiments is that the "no antibody" control should be treated with caution in ChIP assays.

The absolute data presented in FIGS. 2A and 2B were then used to assess the signal/background ratio with the three matrices by calculating the fold enrichment of the specific signals from seven DNA loci to a control with no antibody and two other nonspecific antibody controls which used either IgG or irrelevant antibodies; these results are summarized in Table 2.

Table 2 Fold Enrichment of the Specific Signals from Seven DNA Loci to a No Antibody Control and Two Non-Specific Controls, IgG and Irrelevant Antibodies, in ChIP Experiments (Detailed in FIGS. 2A and 2B) for the Three Matrices.

Fold enrichment values were calculated by dividing the values of the specific signals by one of the three controls and are presented this data in tabular form (values less than 4 are shown in bold italic).

enrichment factor is necessary in a particular ChIP experiment to offer useful information. However these results show that the BioVyon matrix consistently provides greater enrichment than the other two matrices it has been compared with in this investigation.

This comparative investigation also demonstrated that the experimental procedures using the rigid BioVyon Protein A columns were considerably easier to carry out and much quicker than either of the other two formats based on loose beads. The BioVyon devices come ready prepared with a fixed amount of Protein A bound to the rigid porous frit within the column. This immediately removes the potential for dispensing errors associated with adding bead based matrices into the vessels used for the IP process. Moreover, the processing steps associated with the BioVyon columns are, in all cases simpler, the reagents and buffer solutions are held in the column for any incubation period and are then allowed to drain from the column. Chromatin bound to the Protein A is also bound onto the rigid porous frit in the BioVyon column and cannot be lost from the column in any of the processes normally used during IP, whereas the beads must be carefully separated and conserved during all the washing and reagent mixing steps (centrifugation for the Sepharose and magnetic separation for the Dynabeads). This makes the bead based IP processes very time consuming with the potential for bead loss (and hence target loss) at each step in a multistep process.

As an example, an IP process using Sepharose beads, which includes multiple centrifugation, aspiration and re-suspension steps, could take more than three hours. An IP process using Dynabeads, involving several magnetic sepa-

TABLE 2

| Enrichment ratios against each control for all three matrices | | | | | | | |
|---|---|---|---|---|---|---|---|
| | H19 | β-globin | N-Myc | TATA | PLK | DM1 | PIM |
| Enrichment against no Ab | | | | | | | |
| BioVyon | 95.93 | 22.90 | 10.26 | 9.59 | 10.73 | 9.40 | 4.76 |
| Dynabead | 6.90 | *3.23* | 5.52 | *3.90* | 11.48 | 8.53 | 10.19 |
| Sepharose | 9.27 | 13.45 | 6.76 | *1.96* | 19.90 | 28.90 | *1.08* |
| Enrichment against IgG | | | | | | | |
| BioVyon | 41.70 | 18.25 | 16.65 | 8.06 | 6.80 | 4.39 | 4.12 |
| Dynabead | 37.71 | 9.50 | 9.86 | *1.67* | 13.85 | 5.66 | 25.74 |
| Sepharose | 26.79 | 7.89 | 7.42 | 5.93 | *1.78* | *1.81* | *1.77* |
| Enrichment against Irr. Ab | | | | | | | |
| BioVyon | 39.67 | 15.65 | 15.03 | 9.44 | 6.82 | 5.12 | *3.40* |
| Dynabead | 7.67 | 7.28 | *3.45* | *1.69* | 7.98 | 17.50 | 8.60 |
| Sepharose | 12.61 | *3.76* | 9.71 | 17.36 | 6.73 | *2.44* | *1.18* |

Specifically, if we consider a fold enrichment value of four to be a reasonable value necessary for the ChIP assay to be effective, then BioVyon would be effective in 20 of the 21 assays evaluated, Dynabeads would be effective in 16 of the 21 assays evaluated and Sepharose would only be effective in 13 of the 21 assays evaluated (enrichment values below 4 in Table 2 are shown in italic for clarity). Put another way virtually any level of DNA enrichment (a value greater than 1) shows the BioVyon™-Protein A to be more effective than the two bead based matrices when a comparison is made across all 21 assays. Given the complex nature of the ChIP assay, it is difficult to determine what fold ration steps (aspiration and resuspension), could take more than 30 minutes. In comparison an IP process using. BioVyon takes 10 to 15 minutes, requires fewer washing steps (3 for each buffer instead of 6 for each buffer for the beads) and requires no separation or resuspension, consequently it does not run the same risk of target loss during the overall process.

In addition, the above experimentation suggests that a pre-blocking step is also unnecessary in the BioVyon protocol further simplifying the process and removing another step associated with a bead based matrix that requires bead manipulation and the potential for target loss. It is also important to note that "ChIPped" DNA fragments are very sensitive to nuclease activity and so any reduction in the overall processing time will decrease the possibility of DNA degradation by nucleases.

In summary, the BioVyon matrix offers greater DNA pull down, improved enrichment performance and ease of use with fewer processing steps thereby reducing the likelihood of operational errors that could cause target losses. These properties of BioVyon are very valuable for the development of the micro ChIP applications and also automation of ChIP assays [26; 27; 28; 29]. We therefore conclude that BioVyon™-Protein A can be considered a very attractive alternative to bead based matrices for use in ChIP and other IP based assays being easier and quicker to use with less potential for error.

Example 2

In this example, ChIP assays were carried out using a single antibody raised against RNA polymerase II and single loci, human GAPDH, as the target gene for Q-PCR analysis. Initial comparisons conducted focussed on the adjustment of a recommended optimal ChIP protocol where magnetic beads were substituted with BioVyon gravity flow columns at the immunoprecipitation step. The results show that the BioVyon-protein A gravity flow columns are significantly more suitable supports for IP than their currently used magnetic bead counterparts. In further experiments the gravity flow columns were replaced by spin columns to further improve the assay.

Materials and Methods
Cell Culture and Fixation

Secondary human breast carcinoma cell lines MCF-7 were obtained and seeded at a density of $7.5 \times 10^6$ onto round plastic 14 cm Petri dishes (Invitrogen). Grown in 10% stripped serums DMEM (Gibco), the cells reached 80-100% confluency ($15 \times 10^6$ cells) after 24 hrs and were immersed in 20 ml of 1% Formaldehyde for 10 mins at room temperature. Chromatin was extracted and prepared through sonication for immunoprecipitation.

Comparison of ChIP Using BioVyon-Protein A Gravity Flow and Spin Columns with Protein G Magnetic Beads The fragmented chromatin samples were adjusted to 10 µg/µl then subjected to immunoprecipitation using RNA polII specific rabbit polyclonal antibody (0.8 µg/µl) or normal unconjugated rabbit IgG as a negative control. The recovered DNAs were analysed in triplicate by Q-PCR. The method using protein G magnetic beads was conducted using the recommended protocol, and compared to the method using BioVyon-protein A using optimized buffer composition (see e.g. Example 1 above). The chromatin immunoprecipitation slurries were incubated on the BioVyon columns for 1 hr following 3 hr incubation at 4° C. on an end to end rotor.

BioVyon Spin Column

The BioVyon-protein A matrix was fitted to small plastic spin tubes (Sigma), see FIG. 6C, and housed in a 2 ml collection tube to facilitate the use of centrifugal force to draw the buffer and immunoprecipitation solutions through the columns as opposed to gravity flow. A hydrophobic fit (a rigid porous matrix comprising sintered polyethylene particles) was placed beneath the BioVyon-protein A fit in the column to remove any flow through occurring both before and after centrifugal force was applied.

In both gravity flow and spin column methods the fragmented chromatin samples were adjusted to 10 µg/µl and subjected to immunoprecipitation using RNA pol II specific rabbit polyclonal antibody (0.8 µg/µl) or normal unconjugated rabbit IgG as a negative control. The recovered DNAs were analysed in triplicate by Q-PCR. The immunoprecipitation and washing step of the BioVyon-protein A optimal protocol were performed on a spin column using a centrifugal force of 10000 rpm for 30 s; the immunoprecipitation slurries were again incubated on a rotor for 3 hrs and then applied to the diluted column for a further 1 hr.

Effect of Hydrophobic Frit

In a separate experiment two spin column variations were tested, one where a hydrophobic frit was placed beneath the protein A column to remove any flow through occurring and a second without a frit. The size of the frit was 7.2 mm diameter for the spin columns.

The fragmented chromatin samples were adjusted to 10 µg/µl and subjected to immunoprecipitation using RNA pol II specific rabbit polyclonal antibody (0.8 µg/µl) or normal unconjugated rabbit IgG as a negative control. The recovered DNAs were analysed in triplicate by QRT-PCR. The immunoprecipitation slurries were again incubated on a rotor for 3 hrs and then applied to the washed column for a further 1 hr. The immunoprecipitation and washing steps of the BioVyon-protein A spin columns were performed using a centrifugal force of 1000 rpm for 30 s.

Results

Figure 8:
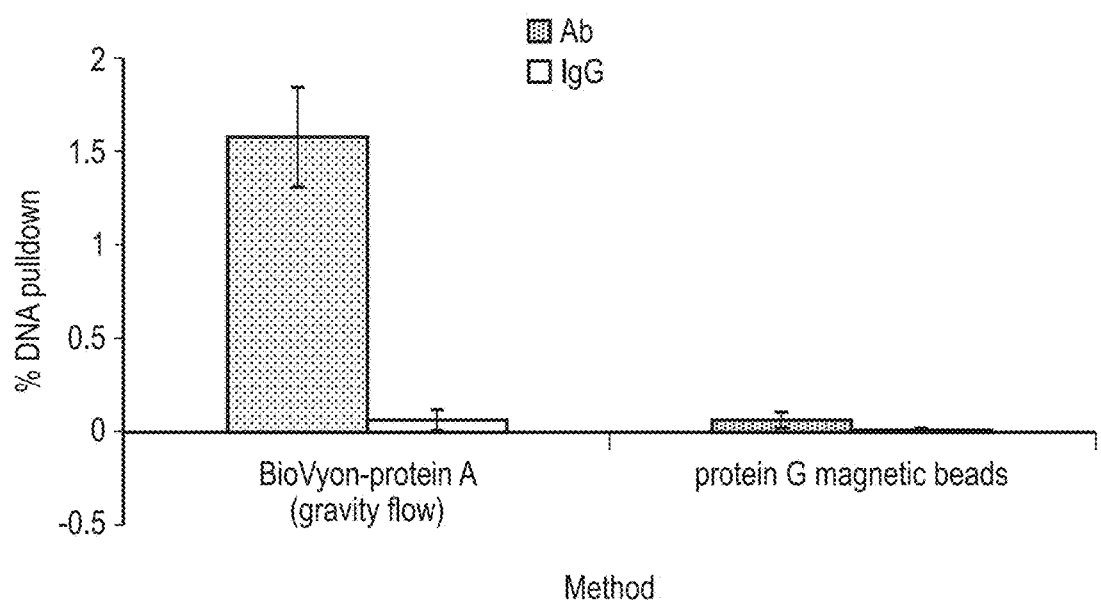
FIG. 8: ChIP signal obtained using BioVyon-protein A (in a gravity flow column) compared directly to protein G magnetic beads. When compared directly, using the same input sample and concentration chromatin, the BioVyon-protein A method resulted in about a 25 fold increase in % DNA pull down.

Comparison of ChIP Using BioVyon-Protein A Gravity Flow Columns and Protein G Magnetic Beads The optimal BioVyon-protein A method, when compared to the optimal ChIP protocol using protein G magnetic beads, compared favourably in terms of the signal pull-down achieved. Under optimal conditions, the BioVyon-protein A protocol resulted in about a 25 fold increase in the % DNA pull-down using the exact same sample of MCF7 breast cancer cells, targeting the RNA polymerase II protein bound to the GAPDH target gene (see FIG. 8). This represents a significant increase in ChIP signal and a significant improvement on a current market leading protocol for ChIP investigations.

BioVyon Spin Column Method

The adaptation of the gravity flow columns to spin columns may facilitate easier handling of the columns during the ChIP protocols, and could increase the signal pull-down. The more secure spin washes, in terms of catching any flow through the columns which may have been lost using gravity flow, is thought to be a major factor in the enhancing the efficiency of this method.

Figure 9:
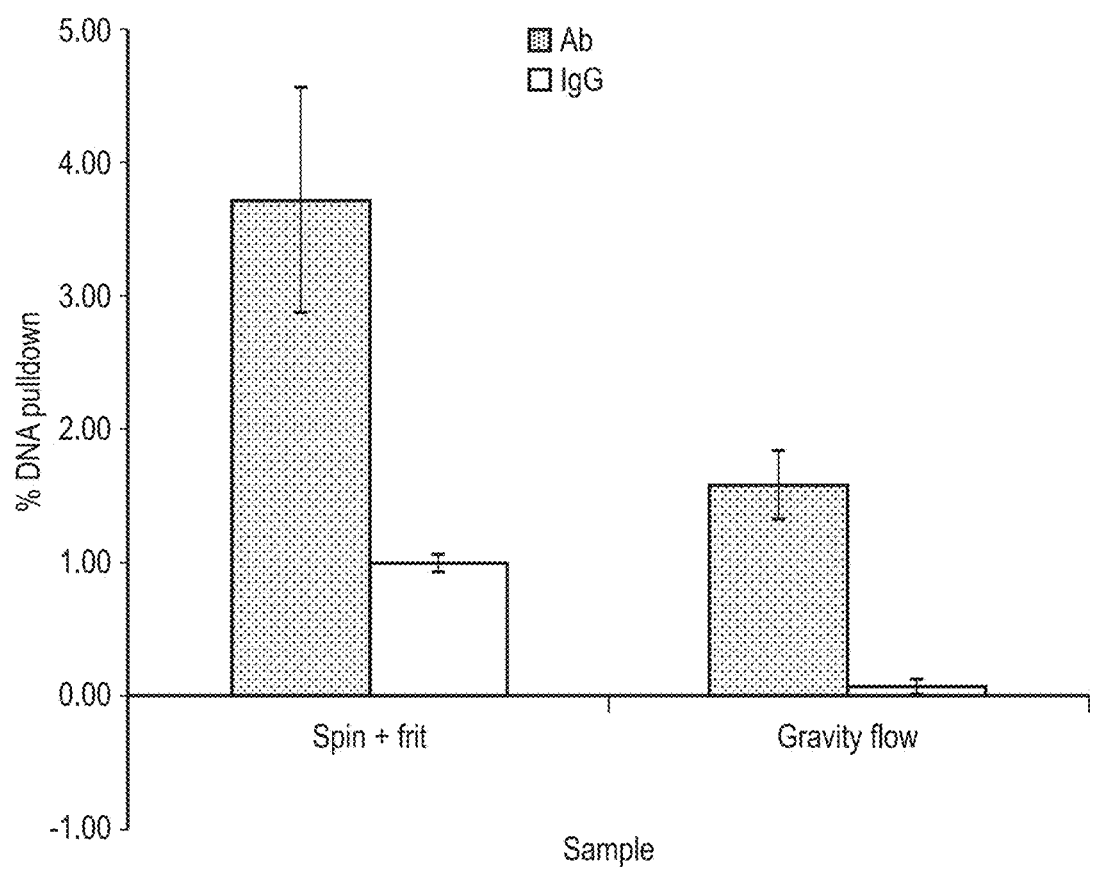
FIG. 9. BioVyon protein A spin column performance against gravity flow column performance. The use of a spin column with a hydrophobic frit enabled successful transition from a gravity flow column assay to a spin column assay. When immobilised alongside a hydrophobic frit and used as a spin column the BioVyon protein A method resulted in a 2.3 fold increase in % DNA pull down when compared to their gravity flow counterparts using exactly the same DNA template sample and antibody concentration.

FIG. 9 shows that the use of a spin column including a hydrophobic frit enabled successful transition from a gravity flow assay to a spin column assay. When immobilised alongside a hydrophobic fit and used as a spin column the BioVyon protein A method resulted in a 2.3 fold increase in % DNA pull down when compared to their gravity flow counterparts using exactly the same DNA template sample and antibody concentration.

Effect of Hydrophobic Frit

In a separate experiment two spin column variations were tested, one where a hydrophobic frit was placed beneath the BioVyon-protein A frit in the column to remove any flow through occurring and a second without a hydrophobic frit.

Figure 10:
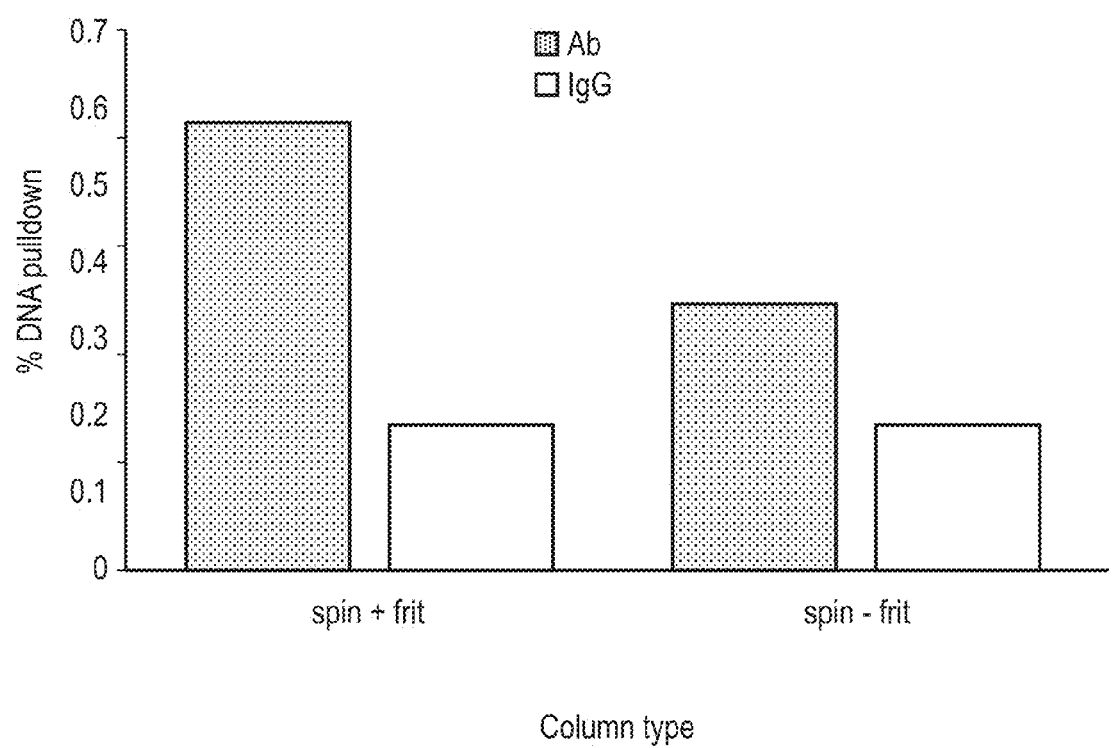
FIG. 10. Hydrophobic frit effect on the performance of the BioVyon spin columns. Specific (Ab) and background (IgG) signal in terms of % DNA pulldown was compared in the case of a spin column with a hydrophobic frit and a spin column without hydrophobic frit.

FIG. 10 shows the effect of a hydrophobic frit effect on the performance of the BioVyon spin columns. When using a hydrophobic frit, the % DNA pull-down in the presence of the antibody is much greater than the IgG (control) sample and thus the enrichment ratio is improved.

REFERENCES

[1] O. Aparicio, J. V. Geisberg, and K. Struhl, Chromatin immunoprecipitation for determining the association of proteins with specific genomic sequences in vivo. Curr Protoc Cell Biol Chapter 17 (2004) Unit 17 7.

[2] C. E. Massie, and I. G. Mills, ChIPping away at gene regulation. EMBO Rep 9 (2008) 337-43.

[3] P. Dasgupta, and S. P. Chellappan, Chromatin immunoprecipitation assays: molecular analysis of chromatin modification and gene regulation. Methods Mol Biol 383 (2007) 135-52.

[4] P. Collas, and J. A. Dahl, Chop it, ChIP it, check it: the current status of chromatin immunoprecipitation. Front Biosci 13 (2008) 929-43.

[5] M. H. Kuo, and C. D. Allis, In vivo cross-linking and immunoprecipitation for studying dynamic Protein:DNA associations in a chromatin environment. Methods 19 (1999) 425-33.

[6] D. S. Hage, Affinity chromatography: a review of clinical applications. Clin Chem 45 (1999) 593-615.

[7] J. Wu, L. T. Smith, C. Plass, and T. H. Huang, ChIP-chip comes of age for genomewide functional analysis. Cancer Res 66 (2006) 6899-902.

[8] M. L. Bulyk, DNA microarray technologies for measuring protein-DNA interactions. Curr Opin Biotechnol 17 (2006) 422-30.

[9] D. Schmidt, M. D. Wilson, C. Spyrou, G. D. Brown, J. Hadfield, and D. T. Odom, ChIP-seq: Using high-throughput sequencing to discover protein-DNA interactions. Methods (2009).

[10] I. Chernukhin, S. Shamsuddin, S. Y. Kang, R. Bergstrom, Y. W. Kwon, W. Yu, J. Whitehead, R. Mukhopadhyay, F. Docquier, D. Farrar, I. Morrison, M. Vigneron, S. Y. Wu, C. M. Chiang, D. Loukinov, V. Lobanenkov, R. Ohlsson, 17 and E. Klenova, CTCF interacts with and recruits the largest subunit of RNA polymerase II to CTCF target sites genome-wide. Mol Cell Biol 27 (2007) 1631-48.

[11] S. Cuddapah, R. Jothi, D. E. Schones, T. Y. Roh, K. Cui, and K. Zhao, Global analysis of the insulator binding protein CTCF in chromatin barrier regions reveals demarcation of active and repressive domains. Genome Res 19 (2009) 24-32.

[12] V. Parelho, S. Hadjur, M. Spivakov, M. Leleu, S. Sauer, H. C. Gregson, A. Jarmuz, C. Canzonetta, Z. Webster, T. Nesterova, B. S. Cobb, K. Yokomori, N. Dillon, L. Aragon, A. G. Fisher, and M. Merkenschlager, Cohesins functionally associate with CTCF on mammalian chromosome arms. Cell 132 (2008) 422-33.

[13] S. R. Frank, M. Schroeder, P. Fernandez, S. Taubert, and B. Amati, Binding of c-Myc to chromatin mediates mitogen-induced acetylation of histone H4 and gene activation. Genes Dev 15 (2001) 2069-82.

[14] D. Toniolo, M. Filippi, R. Dono, T. Lettieri, and G. Martini, The CpG island in the 5' region of the G6PD gene of man and mouse. Gene 102 (1991) 197-203.

[15] R. Ohlsson, R. Renkawitz, and V. Lobanenkov, CTCF is a uniquely versatile transcription regulator linked to epigenetics and disease. Trends Genet 17 (2001) 520-7.

[16] E. M. Klenova, H. C. Morse, 3rd, R. Ohlsson, and V. V. Lobanenkov, The novel BORIS+CTCF gene family is uniquely involved in the epigenetics of normal biology and cancer. Semin Cancer Biol 12 (2002) 399-414.

[17] G. N. Filippova, Genetics and epigenetics of the multifunctional protein CTCF. Curr Top Dev Biol 80 (2008) 337-60.

[18] T. H. Kim, Z. K. Abdullaev, A. D. Smith, K. A. Ching, D. I. Loukinov, R. D. Green, M. Q. Zhang, V. V. Lobanenkov, and B. Ren, Analysis of the vertebrate insulator protein CTCF-binding sites in the human genome. Cell 128 (2007) 1231-45.

[19] M. Lutz, L. J. Burke, P. LeFevre, F. A. Myers, A. W. Thorne, C. Crane-Robinson, C. Bonifer, G. N. Filippova, V. Lobanenkov, and R. Renkawitz, Thyroid hormone-regulated enhancer blocking: cooperation of CTCF and thyroid hormone receptor. Embo J 22 (2003) 1579-87.

[20] G. N. Filippova, C. P. Thienes, B. H. Penn, D. H. Cho, Y. J. Hu, J. M. Moore, T. R. Klesert, V. V. Lobanenkov, and S. J. Tapscott, CTCF-binding sites flank CTG/CAG repeats and form a methylation-sensitive insulator at the DM1 locus. Nat Genet 28 (2001) 335-43.

[21] C. M. Farrell, A. G. West, and G. Felsenfeld, Conserved CTCF insulator elements flank the mouse and human beta-globin loci. Mol Cell Biol 22 (2002) 3820-31.

[22] A. C. Bell, and G. Felsenfeld, Methylation of a CTCF-dependent boundary controls imprinted expression of the Igf2 gene. Nature 405 (2000) 482-5.

[23] D. Takai, F. A. Gonzales, Y. C. Tsai, M. J. Thayer, and P. A. Jones, Large scale mapping of methylcytosines in CTCF-binding sites in the human H19 promoter and aberrant hypomethylation in human bladder cancer. Hum Mol Genet 10 (2001) 2619-26.

[24] A. J. Wilson, D. S. Byun, N. Nasser, L. B. Murray, K. Ayyanar, D. Arango, M. Figueroa, A. Melnick, G. D. Kao, L. H. Augenlicht, and J. M. Mariadason, HDAC4 promotes growth of colon cancer cells via repression of p21. Mol Biol Cell 19 (2008) 4062-75.

[25] J. W. Kim, P. Gao, Y. C. Liu, G. L. Semenza, and C. V. Dang, Hypoxia-inducible factor 1 and dysregulated c-Myc cooperatively induce vascular endothelial growth factor and metabolic switches hexokinase 2 and pyruvate dehydrogenase kinase 1. Mol Cell Biol 27 (2007) 7381-93.

[26] J. A. Dahl, and P. Collas, MicroChIP: chromatin immunoprecipitation for small cell numbers. Methods Mol Biol 567 (2009) 59-74.

[27] J. A. Dahl, A. H. Reiner, and P. Collas, Fast genomic muChIP-chip from 1,000 cells. Genome Biol 10 (2009) R13.

[28] S. Flanagin, J. D. Nelson, D. G. Castner, O. Denisenko, and K. Bomsztyk, Microplate-based chromatin immunoprecipitation method, Matrix ChIP: a platform to study signaling of complex genomic events. Nucleic Acids Res 36 (2008) e17.

[29] A. R. Wu, J. B. Hiatt, R. Lu, J. L. Attema, N. A. Lobo, I. L. Weissman, M. F. Clarke, and S. R. Quake, Automated microfluidic chromatin immunoprecipitation from 2,000 cells. Lab Chip 9 (2009) 1365-70.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A separation column comprising a chamber for holding a liquid sample containing chromatin, and a rigid porous matrix on which a ligand is immobilized, wherein the ligand is capable of binding to a protein associated with the chromatin, and wherein the rigid porous matrix is positioned within the chamber such that, in use, the liquid sample can be passed through the rigid porous matrix, whereby chromatin present in the liquid sample is separated from the liquid sample as it flows through the rigid porous matrix.

2. A separation column according to claim 1, wherein the rigid porous matrix comprises sintered thermoplastic polymer particles.

3. A separation column according to claim 1, wherein the rigid porous matrix is in the form of a filter disc or frit.

4. A separation column according to claim 1, wherein the rigid porous matrix is positioned above an effluent port of the column, such that the liquid sample held in the chamber can be passed through the rigid porous matrix and exit the column, thereby isolating chromatin from the liquid sample by binding of chromatin to the rigid porous matrix.

5. A separation column according to claim 1, further comprising a collection vessel for receiving liquid which has passed through the rigid porous matrix and exited the column.

6. A separation column according to claim 1, further comprising a hydrophobic matrix.

7. A separation column according to claim 1, wherein the hydrophobic matrix is positioned between the rigid porous matrix and an effluent port of the column.

8. A separation column according to claim 1, which is a spin column.

9. A separation column according to claim 1, wherein the ligand comprises an immunoglobulin, protein A or protein G.

10. A separation column according to claim 1, wherein the rigid porous matrix comprises a modified surface produced by chemical oxidation.

11. A separation column according to claim 10, wherein the modified surface is produced by treatment with one or more oxidizing acids.

12. An array comprising a plurality of separation columns according to claim 1.

13. An array according to claim 12, in the form of a multiwell plate or filtration microplate.

14. A kit comprising a separation column as defined in claim 1, and one or more buffers, solutions or reagents suitable for performing a chromatin immunoprecipitation assay.

15. A method for isolating chromatin from a sample, the method comprising passing a liquid sample containing chromatin through the separation column according to claim 1, whereby the chromatin present in the liquid sample is separated from the liquid sample as it flows through the rigid porous matrix.

16. A method for performing a chromatin immunoprecipitation assay, comprising:
(a) isolating chromatin from a sample according to the method of claim 15; and
(b) recovering DNA from the chromatin.

17. The method of claim 16, further comprising analyzing the DNA recovered from the chromatin.

18. The method of claim 15, wherein the liquid sample containing the chromatin enters the rigid porous matrix at an upper side thereof, flows through the rigid porous matrix and exits the rigid porous matrix at a lower side thereof, wherein the chromatin is separated from the liquid sample as it flows through the rigid porous matrix.

19. The method of claim 15, wherein the separation column comprises an opening at an upper end thereof, and an effluent port at a lower end thereof, the rigid porous matrix being positioned between the opening and the effluent port such that the liquid sample flows through the rigid porous matrix as it passes through the column.

* * * * *